(12) United States Patent
Azam

(10) Patent No.: US 10,512,642 B2
(45) Date of Patent: Dec. 24, 2019

(54) THERAPEUTIC TARGETING OF MYELOPROLIFERATIVE NEOPLASMS BY DUSP1 INHIBITION

(71) Applicant: Children's Hospital Medical Center, Cincinnati, OH (US)

(72) Inventor: Mohammad Azam, Mason, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 15/579,531

(22) PCT Filed: Jun. 3, 2016

(86) PCT No.: PCT/US2016/035815
§ 371 (c)(1),
(2) Date: Dec. 4, 2017

(87) PCT Pub. No.: WO2016/196991
PCT Pub. Date: Dec. 8, 2016

(65) Prior Publication Data
US 2018/0153877 A1 Jun. 7, 2018

Related U.S. Application Data

(60) Provisional application No. 62/170,834, filed on Jun. 4, 2015.

(51) Int. Cl.
| | | |
|---|---|---|
| *A61K 31/4741* | (2006.01) |
| *A61P 35/00* | (2006.01) |
| *A61K 31/137* | (2006.01) |
| *A61K 31/4375* | (2006.01) |
| *A61K 45/06* | (2006.01) |
| *A61K 31/357* | (2006.01) |

(52) U.S. Cl.
CPC ........ *A61K 31/4741* (2013.01); *A61K 31/137* (2013.01); *A61K 31/357* (2013.01); *A61K 31/4375* (2013.01); *A61K 45/06* (2013.01); *A61P 35/00* (2018.01); *A61K 2300/00* (2013.01)

(58) Field of Classification Search
CPC .............. A61K 31/4741; A61K 31/137; A61K 31/357; A61K 31/4375; A61P 35/00
USPC ....................................................... 514/279
See application file for complete search history.

(56) References Cited

U.S. PATENT DOCUMENTS

| | | | |
|---|---|---|---|
| 4,522,811 A | 6/1985 | Eppstein et al. | |
| 9,877,934 B2 * | 1/2018 | Azam ................. | A61K 31/135 |
| 2012/0040855 A1 | 2/2012 | Pan et al. | |
| 2014/0031356 A1 | 1/2014 | Azam et al. | |
| 2014/0113919 A1 | 4/2014 | Baffert et al. | |
| 2015/0148345 A1 | 5/2015 | Lannutti et al. | |

FOREIGN PATENT DOCUMENTS

| | | |
|---|---|---|
| CN | 102764259 A | 11/2012 |
| WO | 2010006291 A1 | 1/2010 |

OTHER PUBLICATIONS

Candas et al. Cancer research, 2014, 74(24), 7498-7509 (Year: 2014).*
Asnafi et al., "Prediction of relapse by day 100 BCR-ABL quantification after allogeneic stem cell transplantation for chronic myeloid leukemia," Leukemia 20(5):793-799, May 2006.
Azam et al., "Activation of tyrosine kinases by mutation of the gatekeeper threonine," Nature Structural and Molecular Biology 15(10):1109-1118, Oct. 2008.
Azam et al., "Activity of dual SRC-ABL inhibitors highlights the role of BCR/ABL kinase dynamics in drug resistance," Proceedings of the National Academy of Sciences 103(24):9244-9249, Jun. 2006.
Azam et al., "Anticipating Clinical Resistance to Target-Directed Agents," Molecular Diagnosis and Therapy 10 (2):67-76, Mar. 2006.
Azam et al., "Mechanisms of Autoinhibition and STI-571/Imatinib Resistance Revealed by Mutagenesis of BCR-ABL," Cell 112(6):831-843, Mar. 2003.
Bartley et al., "Sensitive detection and quantification of minimal residual disease in chronic myeloid leukaemia using nested quantitative PCR for BCR-ABL DNA," International Journal of Laboratory Hematology 32(6p1):e222-228, published online Oct. 26, 2010, print publication Dec. 1, 2010.
Baxter et al., "Acquired mutation of the tyrosine kinase JAK2 in human myeloproliferative disorders," Lancet 365 (9464):1054-1061, Mar. 2005.
Bruennert et al., "Early in vivo changes of the transcriptome in Philadelphia chromosome-positive CD34+ cells from patients with chronic myelogenous leukaemia following imatinib therapy," Leukemia 23(5):983-985, published online Dec. 4, 2008, print publication May 2009.
Corbin et al., "Human chronic myeloid leukemia stem cells are insensitive to imatinib despite inhibition of BCR-ABL activity," The Journal of Clinical Investigation 121(1):396-409, Jan. 4, 2011.
Crossman et al., "hOCT 1 and resistance to imatinib," Blood 106(3):1133-1134, Aug. 1, 2005.

(Continued)

*Primary Examiner* — Yevgeny Valenrod
(74) *Attorney, Agent, or Firm* — Davis Wright Tremaine LLP

(57) ABSTRACT

Methods and compositions disclosed herein generally relate to methods, compounds, and compositions for treating myeloproliferative neoplasms (MPNs) or a symptom thereof, comprising administering, to a subject in need thereof, a therapeutically effective amount of a DUSP1 inhibiting compound, or of a pharmaceutically acceptable salt, ester, solvate, pharmaceutically usable derivative, or prodrug thereof. Embodiments of the invention also relate to use of a compound, or pharmaceutically acceptable salt, ester, solvate, pharmaceutically usable derivative, or prodrug thereof, for the preparation of a composition or medicament for the treatment of a myeloproliferative neoplasm (MPN), wherein the compound is an inhibitor of DUSP1.

20 Claims, 24 Drawing Sheets

(56) References Cited

OTHER PUBLICATIONS

Daley et al., "Blast crisis in a murine model of chronic myelogenous leukemia," Proceedings of the National Academy of Sciences 88(24):11335-11338, Dec. 15, 1991.
Daley et al., "Induction of chronic myelogenous leukemia in mice by the P210bcr/abl gene of the Philadelphia chromosome," Science 247(4944):824-30, Feb. 16, 1990.
Dong et al., "Identification of Small Molecule Inhibitors of Human As(III) S-Adenosylmethionine Methyltransferase (AS3MT)," Chemical Research in Toxicology 28(12):2419-25, Nov. 17, 2015.
Dorfman et al., "Disruption of the erp/mkp-1 gene does not affect mouse development: normal MAP kinase activity in ERP/MKP-1-deficient fibroblasts," Oncogene 13(5):925-931, Sep. 1996.
Druker et al., "Activity of a specific inhibitor of the BCR-ABL tyrosine kinase in the blast crisis of chronic myeloid leukemia and acute lymphoblastic leukemia with the Philadelphia chromosome," New England Journal of Medicine 344 (14): 1038-1042, Apr. 5, 2001.
Druker et al., "Effects of a selective inhibitor of the ABL tyrosine kinase on the growth of BCR-ABL positive cells," Nature Medicine 2(5):561-566, May 1996.
Druker et al., "Efficacy and Safety of a Specific Inhibitor of the BCR-ABL Tyrosine Kinase in Chronic Myeloid Leukemia," New England Journal of Medicine 344(14):1031-1037, Apr. 5, 2001.
Eliel et al., "Stereochemistry of Organic Compounds," Wiley, Sep. 1994, 15 pages.
Flower, "Modelling G-protein-coupled receptors for drug design," Biochimica et Biophysica Acta 1422(3):207-34, Nov. 16, 1999.
Goding, "Monoclonal Antibodies: Prinicples and Practice," Academic Press, p. 104, Dec. 1986.
Gorre et al., "Clinical Resistance to STI-571 Cancer Therapy Caused by BCR-ABL Gene Mutation or Amplification," Science 293(5531):876-880, Aug. 3, 2001.
Heine et al., "The JAK-inhibitor ruxolitinib impairs dendritic cell function in vitro and in vivo," Blood 122(7):1192-1202, Aug. 15, 2013.
Hess et al., "Sustained complete molecular remissions after treatment with imatinib-mesylate in patients with failure after allogeneic stem cell transplantation for chronic myelogenous leukemia: results of a prospective phase II open-label multicenter study," Journal of Clinical Oncology 23(30):7583-7593, Oct. 20, 2005.
Huang et al., "Suppression of c-Jun/AP-1 activation by an inhibitor of tumor promotion in mouse fibroblast cells," Proceedings of the National Academy of Sciences 88(12):5292-5296, Jun. 15, 1991.
International Search Report and Written Opinion dated Sep. 9, 2016, International Patent Application No. PCT/US2016/035815, filed Jun. 3, 2016.
James et al., "A unique clonal JAK2 mutation leading to constitutive signalling causes polycythaemia vera," Nature 434(7037):1144-1148, published online Mar. 27, 2005, print publication Apr. 28, 2005.
Jiang et al., "Instability of BCR-ABL gene in primary and cultured chronic myeloid leukemia stem cells," Journal of the National Cancer Institute, 99(9):680-93, May 2, 2007.
Jiang et al., "Primitive interleukin 3 null hematopoietic cells transduced with BCR-ABL show accelerated loss after culture of factor-independence in vitro and leukemogenic activity in vivo," Blood 100(10):3731-3740, Nov. 15, 2002.
Jiang et al., "Properties of CD34+ CML stem/progenitor cells that correlate with different clinical responses to imatinib mesylate;" Blood 116(12):2112-2121, published online Jun. 23, 2010, print publication Sep. 23, 2010.
Jiang et al., "The Challenges of Targeting Chronic Myeloid Leukemia Stem Cells," Clinical Lymphoma and Myeloma 7 (Supplement 2):S71-80, Mar. 2007.
Kaelin, "The concept of synthetic lethality in the context of anti-cancer therapy," Nature Reviews Cancer 5(9):689-698, Sep. 2005.
Kesarwani et al., "Targeting substrate-site in Jak2 kinase prevents emergence of genetic resistance," Scientific Reports 5:14538, Sep. 30, 2015, 19 pages.

Korotchenko et al., "In vivo structure-activity relationship studies support allosteric targeting of a dual specificity phosphatase," ChemBioChem 15(10):1436-45, Jul. 7, 2014.
Koschmieder et al., "Inducible chronic phase of myeloid leukemia with expansion of hematopoietic stem cells in a transgenic model of BCR-ABL leukemogenesis," Blood 105(1):324-334, Jan. 1, 2005.
Krause et al., "Tyrosine kinases as targets for cancer therapy," New England Journal of Medicine 353(2):172-187, Jul. 14, 2005.
Kravolics et al., "A gain-of-function mutation of JAK2 in myeloproliferative disorders," New England Journal of Medicine 352(17):1779-1790, Apr. 28, 2005.
Levine et al., "Activating mutation in the tyrosine kinase JAK2 in polycythemia vera, essential thrombocythemia, and myeloid metaplasia with myelofibrosis," Cancer Cell 7(4):387-97, Apr. 2005.
Li et al., "Bone marrow microenvironment confers imatinib resistance to chronic myelogenous leukemia and oroxylin A reverses the resistance by suppressing Stat3 pathway," Archives of Toxicology 89(1):121-136, Jan. 1, 2015.
Luo et al., "Principles of cancer therapy: oncogene and non-oncogene addiction," Cell 136(5):823-837, Mar. 6, 2009.
Meyer et al., "CHZ868, a type II JAK2 inhibitor, reverses type I JAK inhibitor persistence and demonstrates efficacy in myeloproliferative neoplasms," Cancer Cell 28(1):15-28, Jul. 13, 2015.
Molina et al., "Zebrafish chemical screening reveals an inhibitor of Dusp6 that expands cardiac cell lineages," Nature Chemical Biology 5(9):680-7, Jul. 5, 2009.
Mullally et al., "Myeloproliferative neoplasm animal models," Hematology/Oncoloby Clinics 26(5):1065-81, Oct. 2012.
Noble et al., "Protein kinase inhibitors: insights into drug design from structure," Science 303(5665):1800-1805, Mar. 19, 2004.
O'Hare et al., "AP24534, a pan-BCR-ABL inhibitor for chronic myeloid leukemia, potently inhibits the T315I mutant and overcomes mutation-based resistance," Cancer Cell 16(5):401-412, Nov. 3, 2009.
O'Hare et al., "Pushing the limits of targeted therapy in chronic myeloid leukaemia," Nature Reviews Cancer 12 (8):513-526, Aug. 2012.
Padhye et al., "Fluorocurcumins as cyclooxygenase-2 inhibitor: molecular docking, pharmacokinetics and tissue distribution in mice," Pharmaceutical Research 26(11):2438-2445, Nov. 1, 2009.
Padhye et al., "New difluoro Knoevenagel condensates of curcumin, their Schiff bases and copper complexes as proteasome inhibitors and apoptosis inducers in cancer cells," Pharmaceutical Research 26(8):1874-1880, Aug. 1, 2009.
Pagliarini et al., "Oncogene addiction: pathways of therapeutic response, resistance, and road maps toward a cure," EMBO reports 16(3):280-296, Mar. 1, 2015.
Park et al., "Inhibition of fos-jun-DNA complex formation by dihydroguaiaretic acid and in vitro cytotoxic effects on cancer cells," Cancer Letters 127(1):23-28, May 15, 1998.
Pavlovsky et al., "Molecular monitoring of imatinib in chronic myeloid leukemia patients in complete cytogenetic remission: does achievement of a stable major molecular response at any time point identify a privileged group of patients? A multicenter experience in Argentina and Uruguay," Clinical Lymphoma, Myeloma & Leukemia 11(3):280-5, Jun. 1, 2011.
Quintas-Cardama et al., "Detection of Dormant Chronic Myeloid Leukemia Clones in the Bone Marrow of Patients in Complete Molecular Remission," Clinical Lymphoma, Myeloma & Leukemia 13(6):681-685, published online Sep. 23, 2013, print publication Dec. 1, 2013.
Quintas-Cardama et al., "Flying under the radar: the new wave of BCR-ABL inhibitors," Nature Reviews Drug Discovery 6(10):834-848, 2007.
Roberts et al., "Targetable kinase-activating lesions in Ph-like acute lymphoblastic leukemia," New England Journal of Medicine 371(11):1005-1015, Sep. 11, 2014.
Ross et al., "How I determine if and when to recommend stopping tyrosine kinase inhibitor treatment for chronic myeloid leukaemia," British Journal of Haematology 166(1):3-11, Jul. 1, 2014.
Roumiantsev et al., "Clinical resistance to the kinase inhibitor STI-571 in chronic myeloid leukemia by mutation of Tyr-253 in the

(56) References Cited

OTHER PUBLICATIONS

Abl kinase domain P-loop," Proceedings of the National Academy of Sciences 99(16):10700-5, Aug. 6, 2002.
Sakamoto et al., "Monitoring twenty-six chronic myeloid leukemia patients by BCR-ABL mRNA level in bone marrow: a single hospital experience," Acta Medica Okayama 65(5):335-342, Oct. 1, 2011.
Savona et al., "Getting to the stem of chronic myeloid leukaemia," Nature Reviews Cancer 8(5):341-350, May 2008.
Sawyers, "Even Better Kinase Inhibitors for Chronic Myeloid Leukemia," New England Journal of Medicine 362 (24):2314-2315, Jun. 17, 2010.
Sawyers, "Opportunities and challenges in the development of kinase inhibitor therapy for cancer," Genes and Development 17(24):2998-3010, Dec. 15, 2003.
Sawyers, "Shifting paradigms: the seeds of oncogene addiction," Nature Medicine 15(10):1158-1161, Oct. 1, 2009.
Sawyers, "Targeted Cancer Therapy," Nature 432(7015):294-297, Nov. 18, 2004.
Schöneberg et al., "Structural basis of G protein-coupled receptor function," Molecular and Cellular Endocrinology 151(1-2):181-93, May 25, 1999.
Scott et al., "v-abl causes hematopoietic disease distinct from that caused by bcr-abl," Proceedings of the National Academy of Sciences 88(15):6506-6510, Aug. 1, 1991.
Sexton, "Recent advances in our understanding of peptide hormone receptors and RAMPS," Current Opinion in Drug Discovery and Development 2(5):440-8, Sep. 1, 1999.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell 2(2):117-125, Aug. 1, 2002.
Sharma et al., ""Oncogenic shock": explaining oncogene addiction through differential signal attenuation," Clinical Cancer Research 12(14):4392s-4395s, Jul. 15, 2006.
Sharma et al., ""Oncogenic Shock": Turning an Activated Kinase against the Tumor Cell," Cell Cycle 5 (24):2878-2880, Dec. 11, 2006.
Sharma et al., "A common signaling cascade may underlie "addiction" to the Src, BCR-ABL, and EGF receptor oncogenes," Cancer Cell 10(5):425-435, Nov. 1, 2006.
Sharma et al., "Oncogene addiction: setting the stage for molecularly targeted cancer therapy," Genes Dev 21 (24):3214-3231, Dec. 15, 2007.
Solimini et al., "Non-oncogene addiction and the stress phenotype of cancer cells," Cell 130(6):986-988, Sep. 21, 2007.
Stella, "Prodrugs: An Overview and Definition." Pro-drugs as Novel Drug Delivery Systems, vol. 14, Chapter 1. 115 pages. American Chemical Society. Jun. 1, 1975.
Straussman et al., "Tumour micro-environment elicits innate resistance to RAF inhibitors through HGF secretion," Nature 487(7408):500-504, Jul. 26, 2012.
Talpaz et al., "Phase I trial of AP24534 in patients with refractory chronic myeloid leukemia (CML) and hematologic malignancies," Journal of Clinical Oncology 28(15_suppl):6511, May 20, 2010.
Tang et al., "Immunosuppressant discovery from Tripterygium wilfordii Hook f: the novel triptolide analog (5R)-5-hydroxytriptolide (LLDT-8)," Acta Pharmacologica Sinica 33(9):1112-8, published online Aug. 27, 2012, print publication Sep. 2012.
Tefferi, "Challenges Facing JAK Inhibitor Therapy for Myeloproliferative Neoplasms," New England Journal of Medicine 3660:844-846, Mar. 1, 2012.
Tefferi, "JAK inhibitors for myeloproliferative neoplasms: clarifying facts from myths," Blood 119(12):2721-2730, Mar. 22, 2012.
Tefferi, "Ruxolitinib targets DCs: for better or worse?," Blood 122(7):1096-1097, Aug. 15, 2013.
Verstovsek et al., "Safety and Efficacy of INCB018424, a JAK1 and JAK2 Inhibitor, in Myelofibrosis," New England Journal of Medicine 363(12)1117-1127, Sep. 16, 2010.
Vogt et al., "The benzo [c] phenanthridine alkaloid, sanguinarine, is a selective, cell-active inhibitor of mitogen-activated protein kinase phosphatase-1," Journal of Biological Chemistry 280(19):19078-86, May 13, 2005.
Weinstein, "Addiction to Oncogenes—the Achilles Heal of Cancer," Science 297(5578):63-64, Jul. 5, 2002.
Wernig et al., "Efficacy of TG101348, a selective JAK2 inhibitor, in treatment of a murine model of JAK2V617F-induced polycythemia vera," Cancer Cell 13(4):311-20, Apr. 8, 2008.
Wilson et al., "Widespread potential for growth-factor-driven resistance to anticancer kinase inhibitors," Nature 487 (7408):505-509, Jul. 26, 2012.
Zhang et al., "Targeting cancer with small molecule kinase inhibitors," Nature Reviews Cancer 9(1):28-39, Jan. 2009.
Zhao et al., "Hedgehog signalling is essential for maintenance of cancer stem cells in myeloid leukaemia," Nature 458 (7239):776-779, Apr. 2009.
Zhou et al., "Total synthesis of novel D-ring-modified triptolide analogues: structure-cytotoxic activity relationship studies on the D-ring of triptolide," Organic & Biomolecular Chemistry 9(9):3176-9, Feb. 15, 2011.
Zhang et al., "C-fos regulates neuronal excitability and survival," Nature Genetics 30(4):416-420, Apr. 2002.

\* cited by examiner

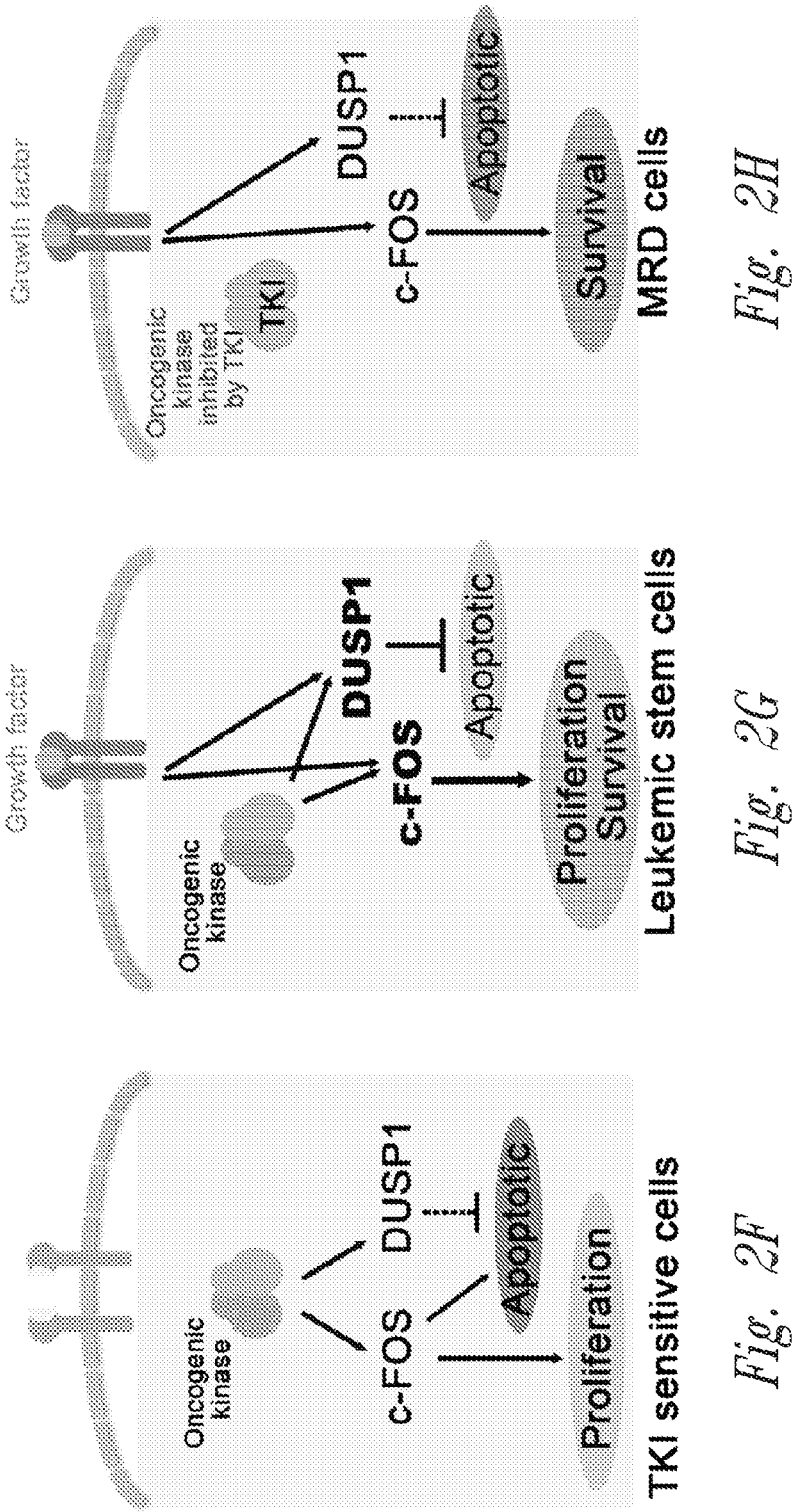

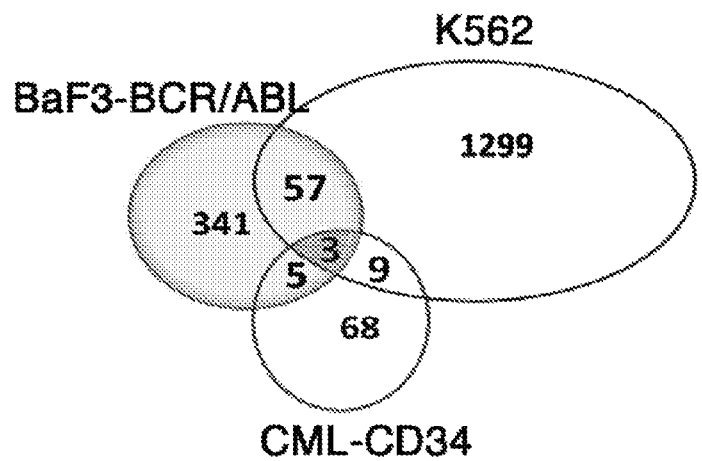
*Fig. 3F*
*Fig. 3G*
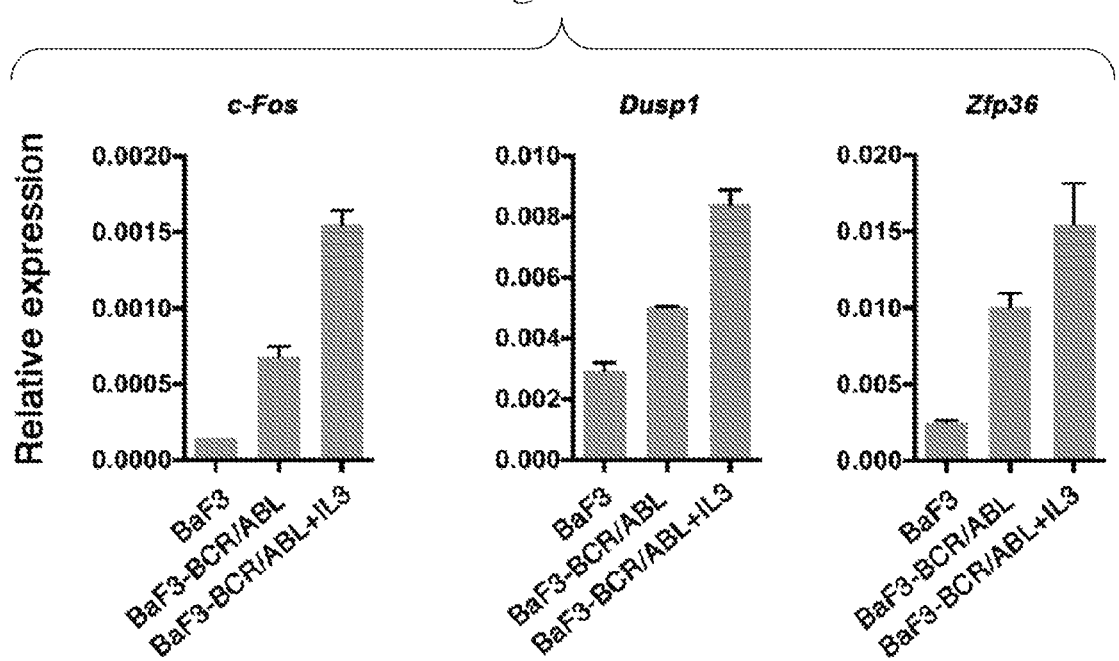

*Fig. 3H*
*Fig. 3I*
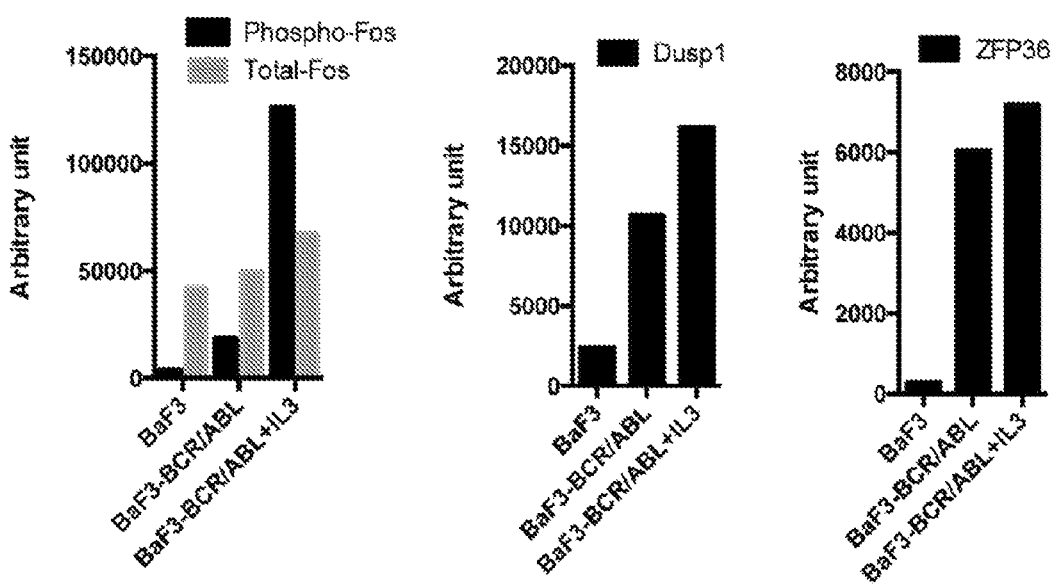

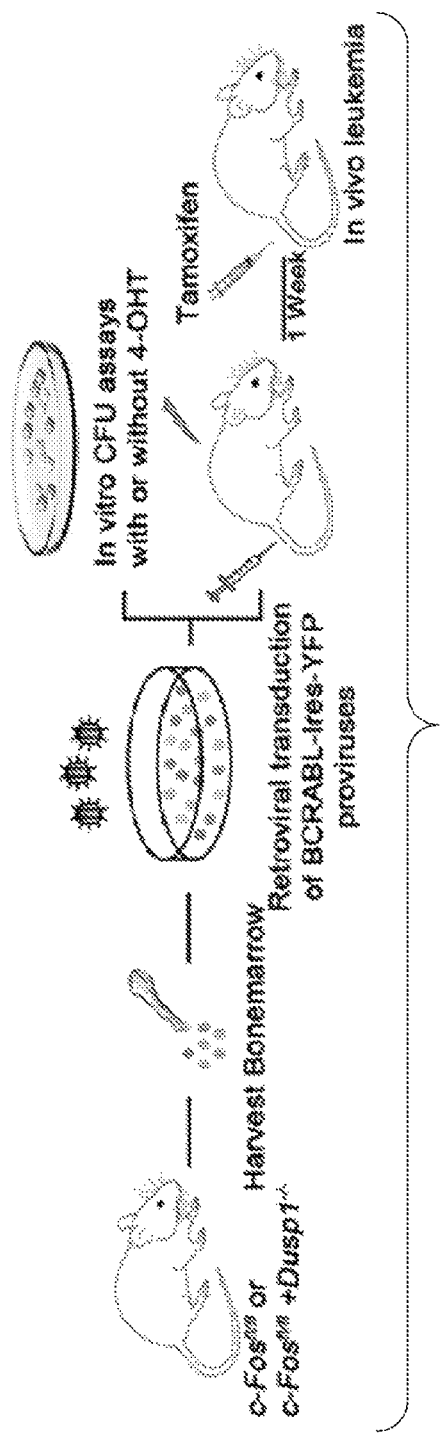
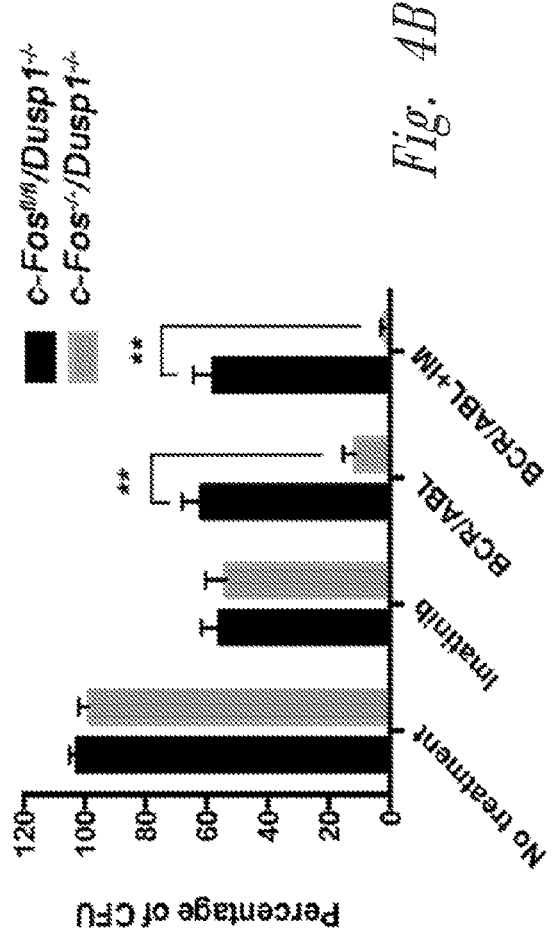
Fig. 4A
Fig. 4B

Overexpression of DUSP1 in MPNs

DUSP1 deficiency is synthetic lethal to MPN driver oncogenes

DUSP1 deficiency is synthetic lethal to MPN driver oncogenes

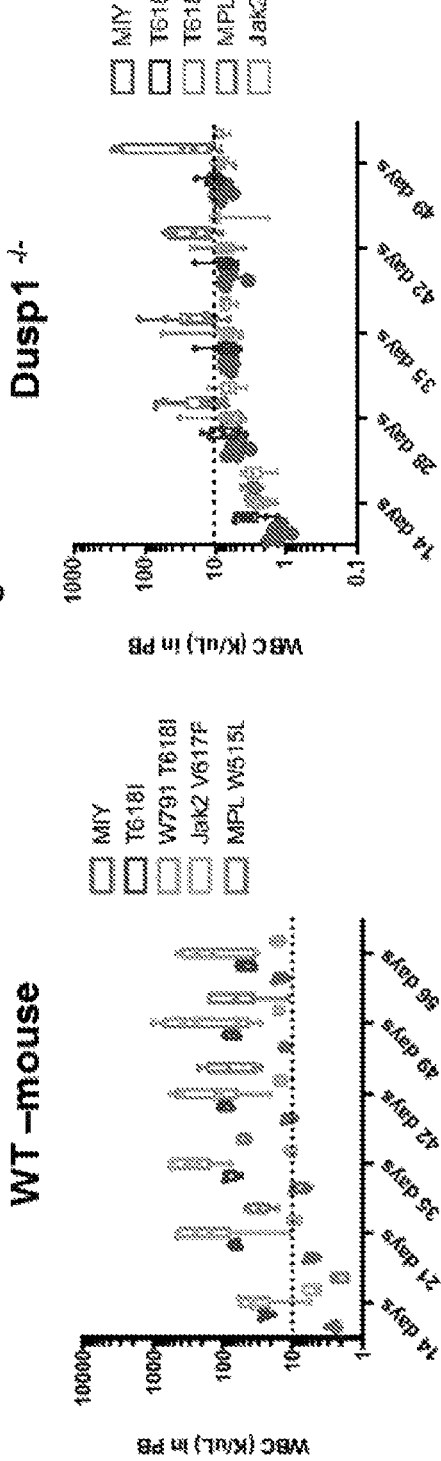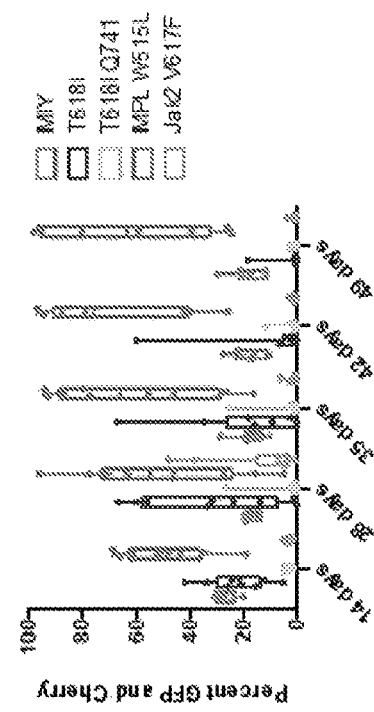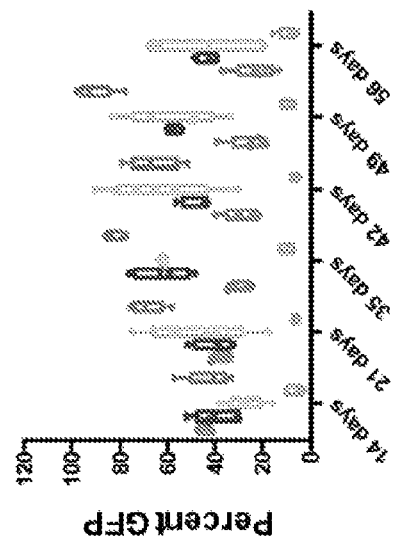
Fig. 12A Fig. 12B Fig. 12C Fig. 12D
DUSP1 deficiency is synthetic lethal to JAK2 and CSF3R oncogenes

Ruxolitinib and BCI eradicate the MPL and CSF3R driven leukemic cells

THERAPEUTIC TARGETING OF MYELOPROLIFERATIVE NEOPLASMS BY DUSP1 INHIBITION

CROSS-REFERENCE TO RELATED APPLICATIONS

The present application is a U.S. National Stage entry under 35 U.S.C. § 371 of International Application No. PCT/US2016/035815, filed on Jun. 3, 2016, designating the United States of America and published in English on Dec. 8, 2016, which in turn claims priority to U.S. Provisional Application No. 62/170,834, filed on Jun. 4, 2015, each of which is hereby incorporated by reference in its entirety.

STATEMENT REGARDING FEDERALLY-SPONSORED RESEARCH

This invention was made with government support under HL114074 awarded by the National Institutes of Health. The government has certain rights in the invention.

FIELD OF THE INVENTION

Particular aspects of the invention disclosed herein generally relate to diagnosis, treatment, and/or management of myeloproliferative disorders, including myeloproliferative neoplasms, and/or conditions arising therefrom and/or related thereto, and in more particular aspects to the use of inhibitors of DUSP1, or of its expression from the Dusp1 gene for treating, and/or management of myeloproliferative disorders, including myeloproliferative neoplasms, and/or conditions arising therefrom and/or related thereto.

BACKGROUND

Myeloproliferative disorders (MPDs), also known as myeloproliferative neoplasms (MPNs), are clonal stem cell disorders characterized by increased production of mature blood cells. MPDs/MPNs are a group of clonal myeloid neoplasms in which a genetic alteration occurs in a hematopoietic progenitor cell leading to its proliferation, resulting in an increase in the peripheral blood white blood cells (WBCs), red blood cells (RBCs), platelets, or a combination of these cells. MPNs are classified as rare diseases.

There are four main MPNs, namely chronic myelogenous leukemia (CML), atypical CML, polycythemia vera (PV), essential thrombocytosis (ET), and primary myelofibrosis (PMF). Additional MPNs include systemic mastocytosis, hypereosinophilic syndrome, chronic myelomonocytic leukemia, chronic neutrophilic leukemia (CNL), and chronic eosinophilic leukemia. In general, leukemia cells can be classified as MPNs.

SUMMARY OF THE INVENTION

Embodiments of the invention relate to methods of treating a myeloproliferative neoplasm (MPN) or a symptom thereof, wherein the methods include administering, to a subject in need thereof, a therapeutically effective amount of one or more DUSP1 inhibiting compounds, or a pharmaceutically acceptable salt, ester, solvate, pharmaceutically usable derivative, or prodrug thereof.

In some embodiments, the compound can be (E)-2-benzylidene-3-(cyclohexylamino)-2,3-dihydro-1H-inden-1-one (BCI), sanguinarine, or an analog or derivative thereof. In some embodiments, the compound can be BCI, BCI-164, BCI-165, BCI-11, BCI-8, BCI-9, BCI-211, BCI-212, BCI-303, BCI-183, BCI-297, BCI-216, BCI-215, BCI-256, BCI-269, BCI-304, BCI-296, BCI-299, BCI-10, sanguinarine, chelerythrine, hydroxychelidonine, berberine, tetrahydroberberine, or protopine, or an analog or derivative thereof.

In some embodiments, the compound can be BCI or an analog thereof. In some embodiments, the BCI and BCI analogues can have the general structure of Formula (I):

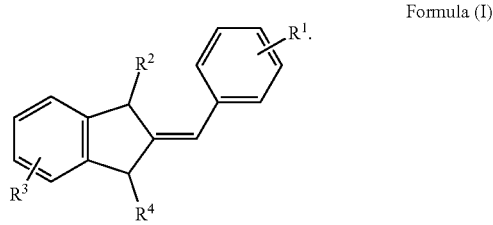

Formula (I)

In compounds having the general structure of Formula (I): $R^1$ can be H, halogen, substituted or unsubstituted straight or branched chain C1-8 alkyl, substituted or unsubstituted straight or branched chain C1-8 heteroalkyl, or —CN; $R^2$ can be —NR'R", wherein R' and R" can optionally be joined together to form a ring; $R^3$ can be H, halogen, substituted or unsubstituted straight or branched chain C1-8 alkyl, substituted or unsubstituted straight or branched chain C1-8 heteroalkyl, or —CN; $R^4$ can be =O or —OH; and R' and R" independently can be H, halogen, substituted or unsubstituted straight or branched chain C1-8 alkyl, substituted or unsubstituted straight or branched chain C1-8 heteroalkyl, substituted or unsubstituted C3-8 cycloalkyl, substituted or unsubstituted C3-8 heterocycloalkyl, or substituted or unsubstituted C5-12 heteroaryl.

In some embodiments, the compound can be sanguinarine or an analog thereof. In some embodiments, the sanguinarine and sanguinarine analogues can have the general structure of Formula (II):

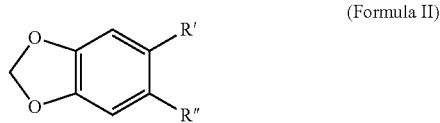

(Formula II)

In compounds having the general structure of Formula (II): R' and R" can be joined in a ring fused to the general core structure and can be 1-4 saturated or unsaturated, substituted or unsubstituted fused ring systems fused to the general core structure represented in Formula (II), wherein each ring can include 4-12 atoms, and wherein said atoms of the fused ring systems independently can be carbon, nitrogen, oxygen, silicon, phorphorous, or sulfur, and wherein substituent groups for the fused ring systems independently can be hydrogen, halogen, substituted or unsubstituted straight or branched chain C1-8 alkyl, substituted or unsubstituted straight or branched chain C1-8 heteroalkyl, substituted or unsubstituted C3-8 cycloalkyl, substituted or unsubstituted C3-8 heterocycloalkyl, =O, —OH, or —CN.

In some embodiments, the MPN can include one or more disease or condition selected from the group consisting of chronic myelogenous leukemia (CML), atypical CML, polycythemia vera (PV), essential thrombocytosis (ET), primary myelofibrosis (PMF), chronic neutrophilic leukemia (CNL), systemic mastocytosis, hypereosinophilic syndrome, chronic myelomonocytic leukemia, or chronic eosinophilic leukemia. In some embodiments, the MPN can be chronic myelogenous leukemia (CML), atypical CML, polycythemia vera (PV), essential thrombocytosis (ET), primary myelofibrosis (PMF), or chronic neutrophilic leukemia (CNL).

In some embodiments, the DUSP1 inhibitor can be an inhibitor of the Dusp1 gene and/or the Dusp1 protein.

In some embodiments, the method can further include combination therapy. In some embodiments, the combination therapy can include at least one therapy selected from the group consisting of surgery, chemotherapy, and radiation. In some embodiments, the combination therapy can include administration of at least one additional therapeutic agent to the patient. In some embodiments, the at least one additional therapeutic agent can be a tyrosine kinase inhibitor (TKI). In some embodiments, the at least one additional therapeutic agent can be an inhibitor of c-Fos. In some embodiments, the TKI can be an inhibitor of a tyrosine kinase gene and/or a tyrosine kinase protein. In some embodiments, the c-Fos inhibitor can be an inhibitor of the c-Fos gene and/or the c-Fos protein.

In some embodiments, the at least one additional therapeutic agent is a JAK kinase inhibitor. In some embodiments, the JAK kinase inhibitor can be selected from the group consisting of ruxolitinib, CYT387, BMS911543, SAR302503BBT594, TG101348, CHZ868, and pacritinib, and analogs and derivatives thereof.

In some embodiments, the at least one additional therapeutic agent is a MKP inhibitor. In some embodiments, the MKP inhibitor can be selected from the group consisting of sanguinarine, chelerythrine, hydroxychelidonine, berberine, tetrahydroberberine, protopine, and NSC-95397, and analogs and derivatives thereof.

In some embodiments, the at least one additional therapeutic agent can be a PTP inhibitor. In some embodiments, the PTP inhibitor can be selected from the group consisting of TPI-1, TPI-2, TPI-3, TPI-4, TPI-5, TPI-6, TPI-7, TPI-8, TPI-9, TPI-10, TPI-11 triptolide, and (5R)-5-hydroxytriptolide (LLDT-8), and analogs and derivatives thereof.

In some embodiments, the at least one additional therapeutic agent can be hydroxyurea.

In some embodiments, the compound can be administered orally. In some embodiments, the compound can be administered to the subject over a treatment course of up to 10 days, 10 days to one month, one month to 6 months, 6 months to one year, one year to two years, or longer than two years.

In some embodiments, the method can be part of a treatment monitoring protocol. In some embodiments, the treatment monitoring protocol can include obtaining MPN tissue from the patient and analyzing the tissue for DUSP1 activity.

Embodiments of the invention also encompass use of a compound, or pharmaceutically acceptable salt, ester, solvate, pharmaceutically usable derivative, or prodrug thereof, for the preparation of a medicament for the treatment of a myeloproliferative neoplasm (MPN), wherein the compound can be an inhibitor of DUSP1.

Embodiments of the invention also encompass compositions for the treatment of a myeloproliferative neoplasm (MPN), wherein the compositions include an effective amount of a compound, or pharmaceutically acceptable salt, ester, solvate, pharmaceutically usable derivative, or prodrug thereof, wherein the compound can be an inhibitor of DUSP1; and (b) an effective amount of a further medicament active ingredient.

BRIEF DESCRIPTION OF THE DRAWINGS

Those of skill in the art will understand that the drawings, described below, are for illustrative purposes only. The drawings are not intended to limit the scope of the present teachings in any way.

FIG. 12 shows that DUSP1 deficiency has synthetic lethality to JAK2 and CSF3R oncogenes, and therefore to MPD development in mice.

DETAILED DESCRIPTION OF THE INVENTION

Figure 1:
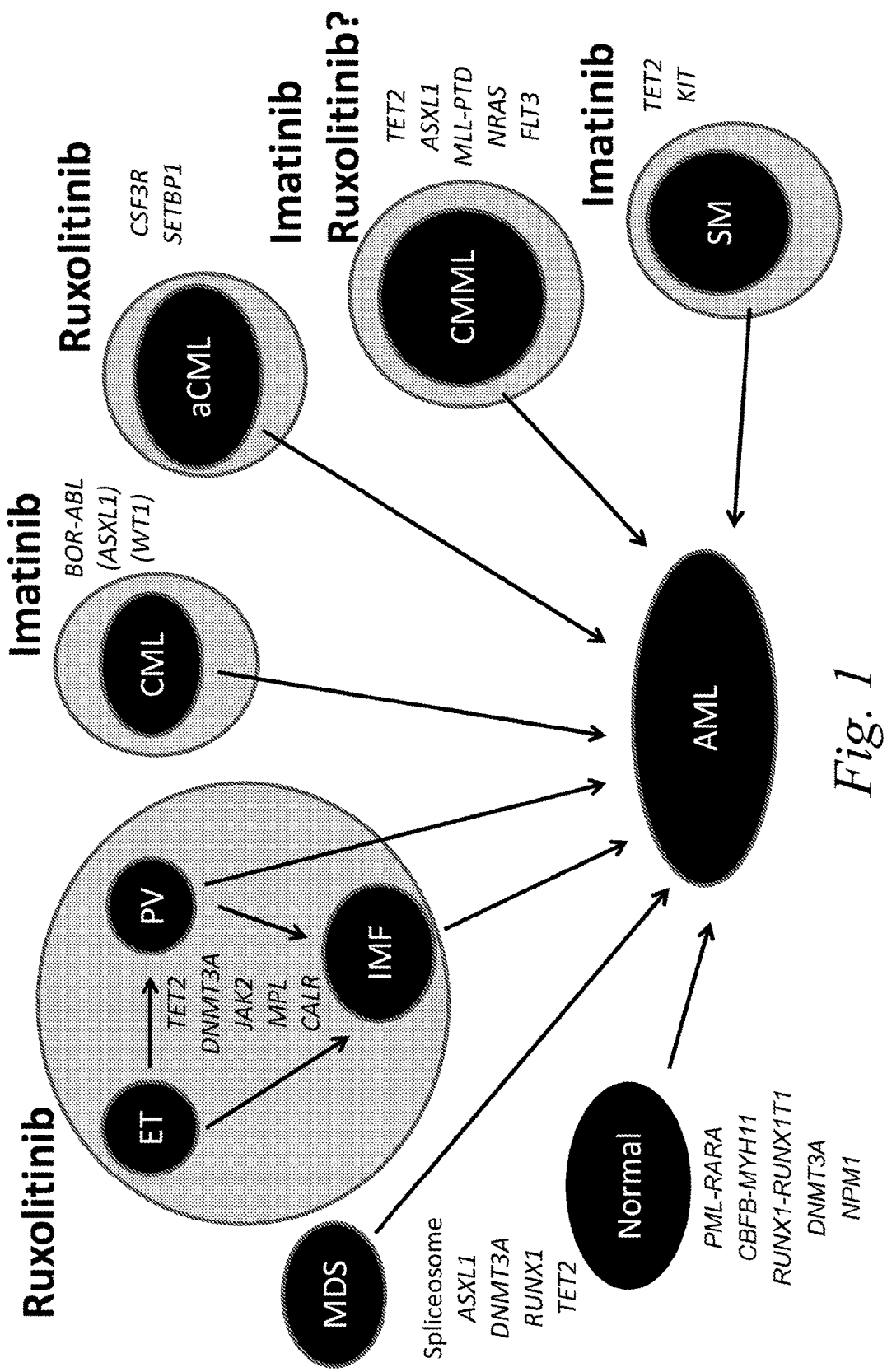
FIG. 1 depicts blood malignancies and TKI response, showing the various conditions that are currently treated using the TKIs ruxolitinib and imatinib.
Figure 2A:
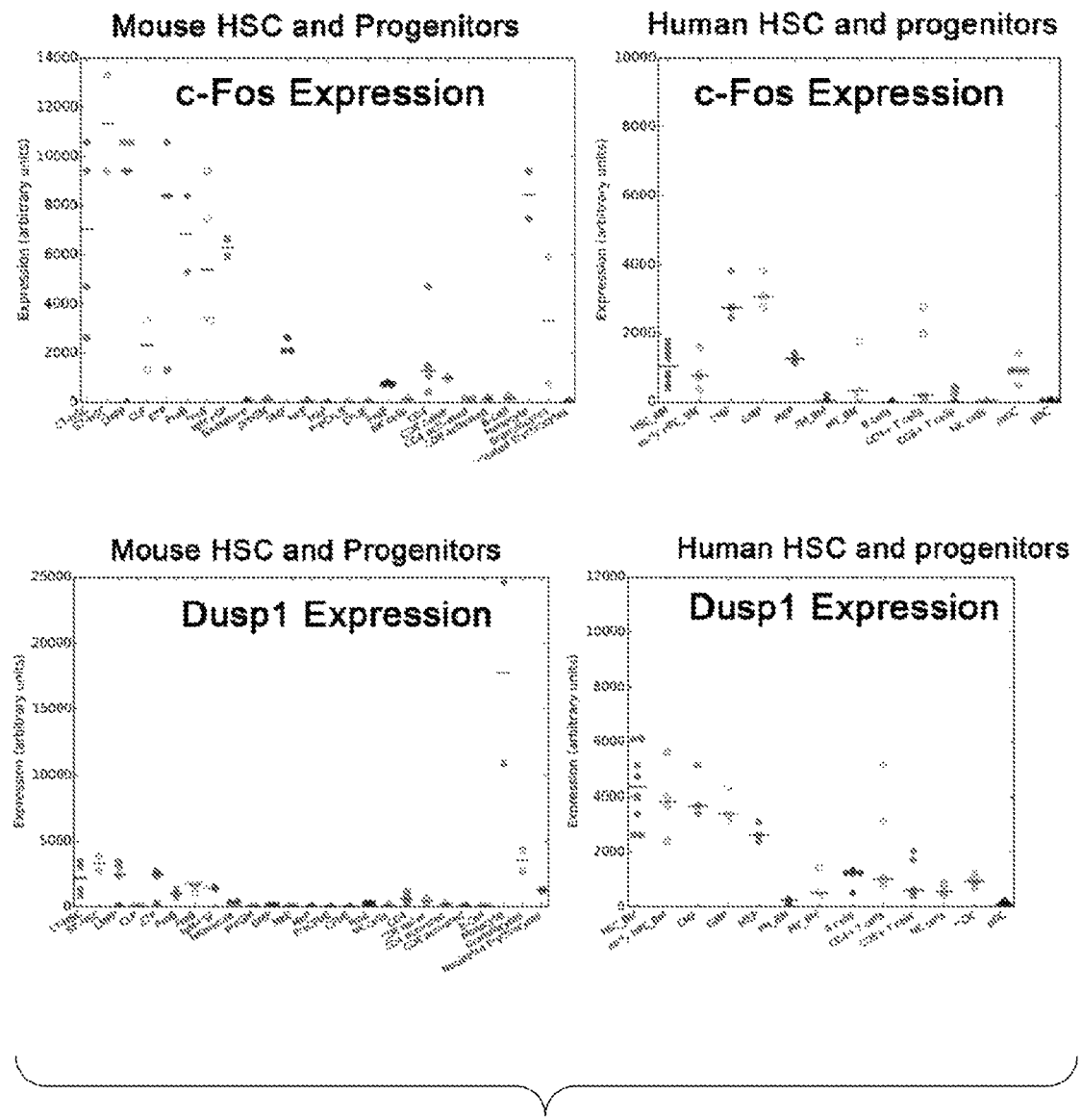
FIG. 2 depicts the mechanism of TKI efficacy in CML as a model system.
Figure 2B:
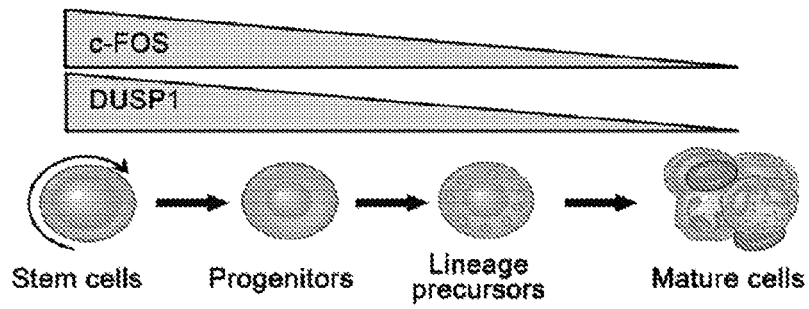
Figure 2C:
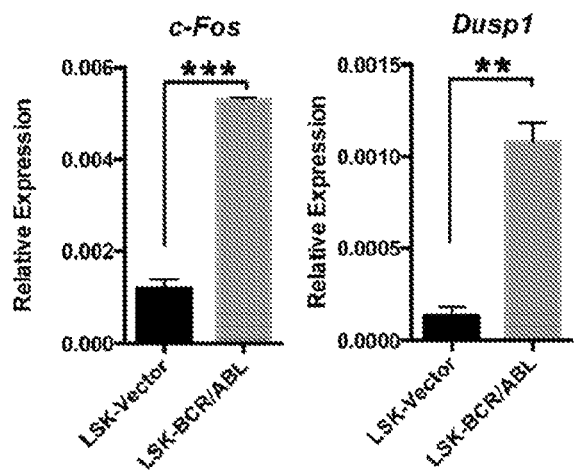
Figure 2D:
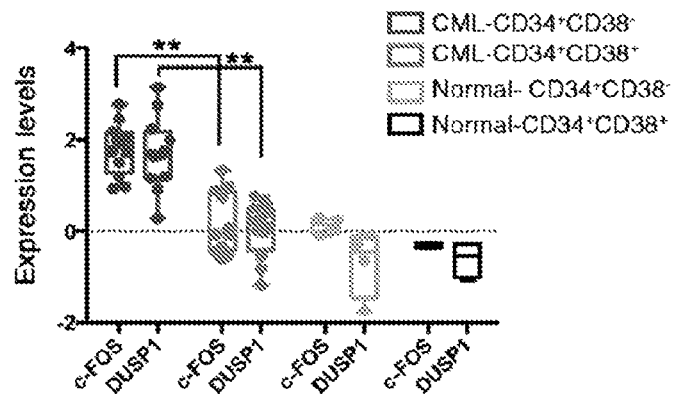
Figure 2E:
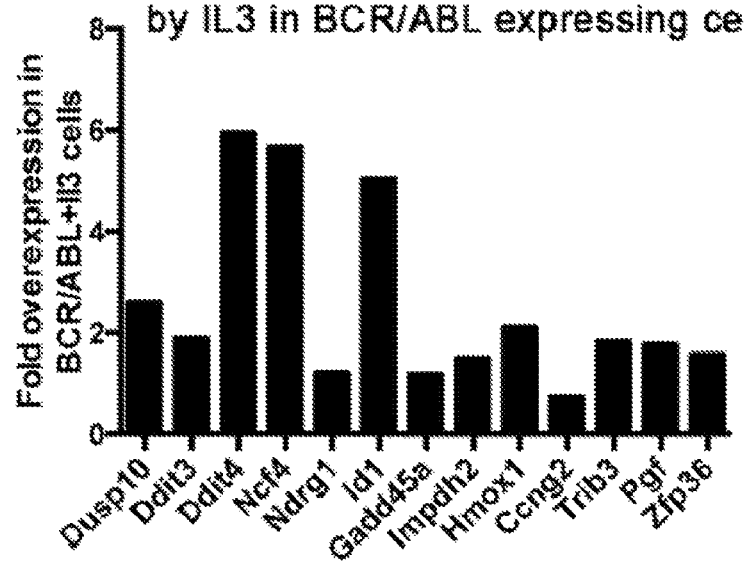
Figure 2E:
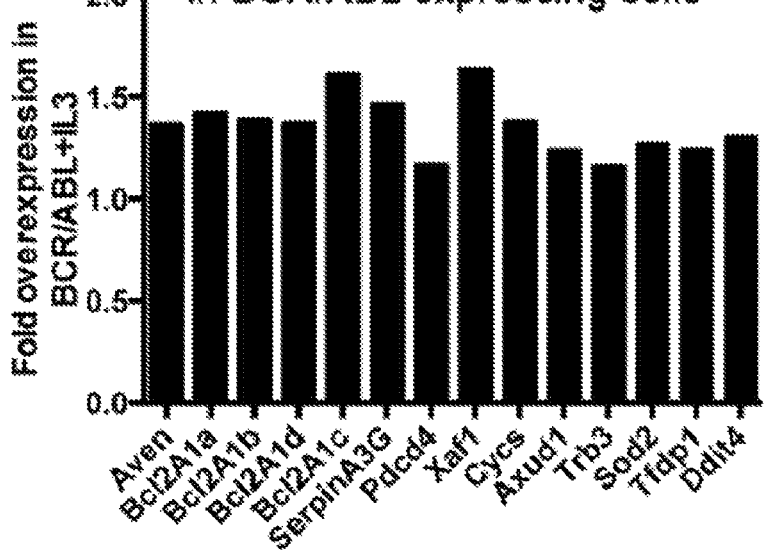

All references cited herein are incorporated by reference in their entirety for their respective teachings.

Unless otherwise noted, terms are to be understood according to conventional usage by those of ordinary skill in the relevant art.

As used herein, the terms "myeloproliferative disorder", "MPD", "myeloproliferative neoplasm", and "MPN" are considered to be equivalent and are thus used interchangably. Any one of these terms can be substituted for any other of these terms.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or microdissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, "blood" can include, for example, plasma, serum, whole blood, blood lysates, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "diagnosing" or "monitoring" with reference to a disease or condition refers to a method or process of determining if a subject has or does not have the disease or condition or determining the severity or degree of disease or condition.

As used herein, the terms "modulated" or "modulation," or "regulated" or "regulation" and "differentially regulated" can refer to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "subject" refers to any member of the animal kingdom. In some embodiments, a subject is a human.

As used herein, the term "diagnosing" or "monitoring" with reference to a disease state or condition refers to a method or process of determining if a subject has or does not have a particular disease state or condition or determining the severity or degree of the particular disease state or condition.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present invention to mitigate a disease or a disorder in a host, preferably in a mammalian subject, more preferably in humans. Thus, the term "treatment" can include includes: preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted (see Webster's Ninth Collegiate Dictionary). Rather, as used herein, the term preventing refers to the ability of the skilled artisan to identify a population that is susceptible to disorders, such that administration of the compounds of the present invention can occur prior to onset of a disease. The term does not mean that the disease state must be completely avoided.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, names for various genes and proteins can relate to the human or murine equivalent, and such terms are used throughout the application interchangably, e.g. JAK2/Jak2, MPL/Mpl, etc.

As used herein, the term "non-oncogene addiction" relates to genes and pathways that are essential to support the oncogenic phenotype of cancer cells but are not required to the same degree for the survival of normal cells. Oncogene addition can therefore reflect that fact that cancer cells also display dependence on classical oncogenes that act in oncogenic pathways. Non-oncogene addiction can therefore reflects the fact that cancer cells display an increased dependence on the normal cellular functions of certain genes that act in oncogenic pathways but are not themselves classical oncogenes. According to particular aspects of the present invention, targeting the genes causing non-oncogene addiction causes synthetic lethality to malignant cells, while sparing normal cells.

Myeloproliferative Disorders and Deficiencies in the Art Relating to Treatment Thereof Myeloproliferative disorders (MPDs), such as myeloproliferative neoplasms (MPNs), are clonal stem cell disorders characterized by increased production of mature blood cells. MPNs are commonly studied via animal models, in particular murine models, which have proven to be an accurate system for modeling human MPN, as known in the art (see, e.g., Mullally et al., *Hematol Oncol Clin North Am* 2012, 26:1065-81).

Philadelphia chromosome-negative MPDs or MPNs (Ph$^-$ MPDs or Ph$^-$ MPNs) consist of polycythemia vera (PV), essential thrombocythemia (ET), primary myelofibrosis (PMF, or MF), and chronic neutrophilic leukemia (CNL). These conditions are commonly treated by administering compounds or compositions which inhibit JAK2, a tyrosine kinase involved in signaling by type II cytokine receptors. The discovery of kinase-activating JAK2 mutations in MPNs provided the rationale for developing tyrosine kinase inhibitors (TKIs) as an MPN treatment strategy, particularly via JAK2 targeting,[1-4] and in 2011, the JAK2 and JAK1 small molecule kinase inhibitor ruxolitinib was approved for the treatment of high-risk PMF, as well as ET and PV. Another TKI, namely imatinib, is used in treating chronic myeloid leukemia (CML). See FIG. 1 for a summary of blood malignancies and TKI response.

Interestingly, MPD induced by mutations in MPL (MPL-W515L) or CSF3R (T681I) was also found to be dependent on JAK2 signaling. Therefore, these Ph-MPDs are now also treated with ruxolitinib. However, unlike imatinib treatment in CML, ruxolitinib treatment does not eliminate the mutant clone, but rather decreases constitutional symptoms and reduces splenomegaly in this population, perhaps by reducing the production of inflammatory cytokines. These clinical studies also revealed that the therapeutic efficacy of ruxolitinib is equally effective in JAK2-V617F positive and negative patients. Given that ruxolitinib is equally effective in JAK2-V617F positive and negative patients, a non-target dependent activity of ruxolitinib is likely.[5,6]

The JAK2 inhibitor ruxolitinib has come to be a first line treatment for MPN patients having myelofibrosis (MF). However, although non-hematologic toxicity induced by ruxolitinib is mild, it causes substantial hematologic toxicity, which includes moderate to severe thrombocytopenia, pancytopenia, and anemia.[7] Jak2 targeting also was found to impart profound neurological toxicities (including peripheral neuropathy and Wernicke encephalopathy), which resulted into termination of two Jak2 inhibitors, namely AZD1480 and fedratinib, from phase III clinical trials. Furthermore, Jak2 inhibition also impairs dendritic cell function, thus resulting in immune suppression and increased infection rates in ruxolitinib-treated patients.[8,9]

Given the toxicity associated with Jak2 inhibitors, many patients are denied for treatment, and only a limited number of patients are eligible for the treatment, namely those who have platelet counts above 100,000/μL. Among the treated patients, the rate of treatment discontinuation is very high (92% after a median time of 9.2 months) in a significant number of patients due to loss of treatment benefit (most patients lost response within 8-12 months of treatment) and drug-induced adverse effects. In addition, a significant number of patients showed severe withdrawal symptoms after treatment discontinuation. This "ruxolitinib withdrawal syndrome" is characterized by an acute relapse of disease symptoms, accelerated splenomegaly, worsening of cytopenias, and occasional hemodynamic decompensation, including a septic shock-like syndrome. Furthermore, ruxolitinib also impairs dendritic cell function that results in immune suppression and increased infection rates in ruxolitinib-treated patients.

Altogether, these studies suggest that therapeutic targeting of JAK2 in MPDs/MPNs is not as effective as was anticipated. Data from JAK2 knock-out mice revealed that the continued inhibition of JAK2 is detrimental to overall survival and maintenance of hematopoietic stem cells, as Jak2 is critical for normal embryonic and hematopoietic development. Thus, prolonged inhibition of Jak2 will be detrimental for normal hematopoietic tissues. These observations warrant identifying additional therapeutic targets in this group of diseases specifically designed to eliminate mutant clones. Accordingly, there is an unmet need to find treatment for this group of MPN patients, and it was reasoned by the present inventors that the identification of additional therapeutic targets, and compounds and compositions targeting the same, would be necessary in order to successfully treat this group of diseases.

Any therapy with the stated goal to successfully treat and possibly eradicate mutant cells and cure cancer must show differential toxicity toward tumor cells relative to normal cells. In this regard, CML represents a valuable paradigm, revealing that the differential toxicity of TKIs is due to the dependence (oncogene-addiction) of leukemic cells on driver oncogenic kinase, where acute inhibition by TKI results into oncogenic shock, causing cell death.[10-12] However, leukemia stem cells (LSCs) in CML are refractory to TKI, suggesting they are not addicted to the oncogene.

Whole Genome Expression Profiling

According to particular aspects, to gain insight into the mechanism of oncogene addiction and how LSCs counter this dependence to develop curative strategy for CML, whole genome expression profiling from BCR/ABL-addicted and non-addicted cells has been performed, as described herein (e.g., see working example 2 below), revealing that c-Fos and Dusp1 are critical mediators of BCR/ABL dependence; c-Fos is a member of the Fos family of transcription factors, and Dusp1 is a member of the dual specificity phosphatase (DUSP) enzyme family, which catalyze the dephosphorylation of proteins on both phosphotyrosine and phosphoserine/phosphothreonine residues within the same substrate. In other words, c-Fos and Dusp1 mediate non-oncogene addiction to BCR/ABL-induced leukemia. Genetic deletion of Dusp1 and c-Fos has synthetic lethality to BCR/ABL expression, and such mice are resistant to develop leukemia. Chemical inhibition of c-Fos and Dusp1 suppressed BCR/ABL-induced leukemia and cured mice of CML. This study revealed that expression levels of c-Fos and Dusp1 determine the threshold of TKI efficacy, such that lower levels of inhibition confer sensitivity, while higher levels of inhibition drive resistance.

The present inventors theorized that MPD cells, like LSCs in CML, might have elevated expression of c-Fos and Dusp1 to counter the TKI induced cell death. The data from mouse MPD models (Jak2-V617F, Mpl-W515L and CSF3R-T618I) and patient samples show an increased expression of Dusp1, but not c-Fos (see FIG. 9, and working example 5). Genetic deletion of Dusp1 has synthetic lethality to MPD development in mouse models. Accordingly, Dusp1 overexpression can mediate non-oncogene addiction in MPD. Therefore, targeting of DUSP1 can have clonal selectivity in MPDs.

Accordingly, for the first time, the study described herein achieves, inter alia, the following: (1) provides evidence for the requirement of Dusp1 in MPDs, (2) establishes Dusp1 as a therapeutic target, and (3) develops therapeutic models and provides evidence for therapeutic targeting by Dusp1 inhibitors, such as the exemplary small molecule inhibitor (E)-2-benzylidene-3-(cyclohexylamino)-2,3-dihydro-1H-inden-1-one (BCI, also known as NSC 150117); such Dusp1 inhibiting compounds can then be used in clinical trials.

Neoplastic cells have extensively rewired pathways for growth and survival that underlie the malignant phenotype. Thus, a key to successful therapy is the identification of critical, functional nodes in the oncogenic network whose inhibition will result in system failure, that is, the cessation of the tumorigenic state by apoptosis, necrosis, senescence, or differentiation. To identify a critical node in MPN, a comprehensive expression analysis was performed (e.g., see working example 2) on bone marrow cells expressing Jak2-V617F, Mpl-W515L, CSF3R-T618I, BCR-ABL, and Flt3-ITD. This analysis revealed that MAP kinase phosphatase 1, also known as Dusp1, is overexpressed in all of these MPN cells, except the BCR-ABL positive cells. Mechanistic understanding of cancer therapy has revealed that the cancer cells are addicted to both oncogenes and non-oncogenes (cancer cells display an increased dependence on the normal cellular functions of certain genes that act in oncogenic pathways but are not themselves classical oncogenes). Therefore targeting the genes causing non-oncogene addiction causes synthetic lethality to malignant cells while sparing normal cells. As demonstrated herein, the Dusp1 gene mediates non-oncogene addiction in MPNs.

Accordingly, as described herein, the inventors have identified Dusp1 as a target in MPN, where it mediates non-oncogene dependence. As Dusp1 knockout mice are normal and do not show any notable phenotype, its targeting is not expected to have toxicities in patients. Mice lacking Dusp1 were therefore used to show that MPN-inducing genes, such as Jak2-V617F, Mpl-W515L, and CSF3R-T618I, are unable to induce leukemia. As further described herein, an exemplary small molecule inhibitor of Dusp1, BCI, has been identified and demonstrated to show a selective targeting of MPN cells. The fact that Dusp1 gene knock-outs are effective in preventing MPN, and do not show negative phenotypes, supports a broad scope of DUSP1 inhibitors that can be used to practice aspects of the present invention.

According to particular aspects, BCI can be used for MPN treatment, including via oral administration, and clinical trial data can be obtained. Additional known Dusp1 inhibitors can also be used for MPN treatment, as well as new versions of Dusp1 inhibitors, with improved pharmacokinetics (PK) and pharmacodynamics (PD); such compounds can be evaluated in vitro and in vivo. For example, these compounds can be evaluated in patient samples using mouse xenotransplants.

Non-Oncogene Addiction and Oncogenic Shock.

This research provides a clear molecular model for testing the relatively new concept of "non-oncogene addiction".[55,56] Non-oncogene addiction is defined as genes and pathways that are essential to support the oncogenic phenotype of cancer cells but are not required to the same degree for the survival of normal cells. Therefore, these cancer-cell-unique dependencies will constitute synthetic lethality when targeted. The present work reduces this concept to practice by illustrating non-oncogene addiction targets for therapeutic intervention in CML.

The induction of transformation by an oncogene is thought to shock cells, and the survival of presumptive cancer cells requires them to induce cellular factors to counter this shock, which will then become uniquely required by the cancer cell.[55,57-60] An underlying theme of this work is the apparent requirement for induced expression of DUSP1 is to quench the oncogenic shock induced by aberrant JAK2 signaling. Specifically, working examples 1-9 experimentally determine the requirement for Dusp1 in MPD, induced by Jak2-V617F, Mpl-W515L, and CSF3R-T618I.

Tyrosine Kinase Inhibitor (TKI) Therapy.

TKI therapy is not wholly curative, in large part as a result of TKI resistance due to growth factor signaling and the failure of TKI therapy to eradicate minimal residual disease, among other reasons. Accordingly, continuous treatment is necessary to prevent minimal residual disease (MRD) cells from reconstituting the tumor.[13-17] MRD stem/progenitor cells survive independently from oncogenic kinase signaling through growth factors[18-20]; however, it is not clear whether the growth factors subsume oncoprotein functions in stem/progenitors preselected by the oncogene activity, or if TKI-resistant MRD cells survive using normal growth-factor-dependent stem/progenitor biology. One premise of the present invention is that lack of TKI selectivity in MPD is reminiscent of TKI resistance in MRD/LICs of chronic myeloid leukemia (CML), which is used herein as a model paradigm (see Example 1). In MRD/LIC of CML, resistance is mediated by cytokine/growth factor signaling that maintains essential oncogenic survival signaling (in the absence of active kinase oncoprotein activity). While in CML, both c-FOS and DUSP1 are activated and confer TKI resistance, but in MPD overexpression of DUSP1 is sufficient to block TKI-induced cell death that results in the lack of clonal selectivity when treated with TKI.

Despite the remarkable efficacy of BCR-ABL inhibitors, resistance is common and limits the prospects for cure.[10,27-35] Drug resistance in tumor cells occurs by activating the targets through overexpression or point mutations, by sequestering the drug, or through target-independent means.[28,36] In CML, target reactivation by point mutation of BCR/ABL constitutes more than 80% of drug-resistance cases.[28,37-39] Moreover, although virtually all newly diagnosed patients attain complete cytogenetic remission following imatinib therapy, the vast majority retains residual leukemic clones that are detectable by highly sensitive PCR methods.[40-48]

Even after two decades of imatinib in the clinic, it is not clearly understood how TKI therapy induces cell death. As a result, TKI therapy is not curative. A small population of cancer cells are insensitive to treatment, manifesting as minimal residual disease (MRD).[43] Unfortunately, bulk MRD cells can contain cancer stem cells/leukemia initiating cells; therefore, continuous drug treatment is needed to prevent the MRD cells from reinstating the disease.[18,24] In addition, MRD cells serve as a reservoir to develop TKI resistance by acquiring genetic resistant mutations in targeted gene or activating alternative survival mechanisms.[29,33,49,50] It is important to note that even the most potent kinase inhibitors are ineffective against MRD LICs constituting disease.[43]

Recent studies revealed that growth factor signaling can mediate resistance to TKI therapy in both leukemia and solid organ tumors.[18-20] Although most CML cells are readily killed by TKI, a subset of LICs exhibits chemoresistance and enhanced survival.[13,51,12,13,43] Recent studies measuring minimal residual disease by multi-parameter flow cytometry after TKI therapy support the concept that failure to completely eradicate the LIC leads to eventual relapse.[14,15] LICs survive by paracrine growth factor signaling from the niche.[16-18] This signaling can not only maintain quiescence but also play a central role in chemoresistance by transmitting survival signaling.[19-23]

The failure of these TKI inhibitors to eradicate disease even if they completely silence the kinase oncoprotein,[43,52-54] underlies the importance of the present Applicant's discoveries. In other words, growth factor signaling in LICs abrogates oncogene dependence, thus enabling these cells to be refractory to TKI treatment. Less is known about the functional pathways used by LIC/MRD cells to evade TKI, but seminal examples of growth factor mediated resistance has been clearly demonstrated[18-20] (albeit without accompanying demonstration of a clear mechanism). Thus, the present Applicant's work is consistent with published basic and clinical observations, and the presently described experiments and working examples fill a critical gap in knowledge by providing molecular detail and mechanisms underlying JAK2-TKI efficacy in MPD. Importantly, Applicants' discoveries and methods provide efficacious treatment and/or cure by targeting DUSP1, which confers non-oncogene dependence in MPD.

According to particular aspects of the presently disclosed research, kinase-oncoprotein and growth-factor signaling converge upon c-FOS and DUSP1, and these factors represent molecular signaling nodes which transmit TKI resistance to MRD/LICs. Importantly, c-FOS and DUSP1 also provide new targets for therapeutic intervention to eradicate TKI refractory cells and provide cancer treatment and/or cures. Prior to this work, it was not known or postulated that DUSP1 was overexpressed in MPNs, and thus there was no rationale to target DUSP1, and in fact doing so would have been regarded as likely to be harmful. Due to the unpredictability of the chemical and biological arts, it was only after DUSP1 was identified as being overexpressed in MPNs, in the work described herein, and with validation from the murine model as described herein, that a motivation and strategy could be developed to treat MPNs via DUSP 1 inhibition.

Representative TKIs and Dusp1 Inhibitors.

TKIs include a number of known small molecules, as well as derivatives and analogues thereof. These include, for example, type I kinase inhibitors and type II kinase inhibitors. Exemplary inhibitors include JAK inhibitors (JAK1 and/or JAK2 inhibitors), such as the small molecules ruxolitinib, CYT387, BMS911543, SAR302503BBT594, TG101348, CHZ868, analogues of any of these compounds, and the like (see, e.g. Wernig et al., *Cancer Cell* 2008 13:311-320; Meyer et al., *Cancer Cell* 2015 28:15-28); protein kinase phosphatase-1 inhibitors, including Dusp1 and/or mitogen-activated protein kinase phosphatase (MKP, e.g. MKP-1) and/or protein tyrosine phosphatase (PTP) inhibitors, such as BCI, sanguinarine, TPI, triptolide, analogues of any of these compounds, and the like (see, e.g., Vogt et al., *J Biol Chem* 2005, 280:19078-86; Korotchenko et al., *Chem Bio Chem* 2014 15:1436-45; Molina et al., *Nature Chemical Biology* 2009 5:680-7), and others; for example, sanguinarine analogues include chelerythrine, hydroxychelidonine, berberine, tetrahydroberberine, protopine, and the like (Vogt et al., *J Biol Chem* 2005, 280: 19078-86, and others), while BCI analogues include BCI-164, BCI-165, BCI-11, BCI-8, BCI-9, BCI-211, BCI-212, BCI-303, BCI-183, BCI-297, BCI-216, BCI-215, BCI-256, BCI-269, BCI-304, BCI-296, BCI-299, BCI-10, and the like (Korotchenko et al., *Chem Bio Chem* 2014 15:1436-45, and others), while TPI analogues include TPI-1, TPI-2, TPI-3, TPI-4, TPI-5, TPI-6, TPI-7, TPI-8, TPI-9, TPI-10, TPI-11, and the like (Dong et al., *Chem Res Toxicol* 2015 28:2419-25, and others), while triptolide analogues include (5R)-5-hydroxytriptolide (LLDT-8), and the like (Tang et al., *Acta Pharmacol Sin* 2012 33:1112-8; Zhou et al., *Org Biol Chem* 2011:9:3176-9, and others). Such compounds are known or can be contemplated by those skilled in the art.

In some embodiments, the BCI and BCI analogues have the general structure of Formula (I):

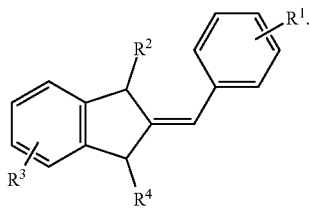

Formula (I)

In compounds of Formula (I), $R^1$ can be H, halogen, substituted or unsubstituted straight or branched chain C1-8 alkyl, substituted or unsubstituted straight or branched chain C1-8 heteroalkyl, or —CN; $R^2$ can be —NR'R", wherein R' and R" can optionally be joined together to form a ring; $R^3$ can be H, halogen, substituted or unsubstituted straight or branched chain C1-8 alkyl, substituted or unsubstituted straight or branched chain C1-8 heteroalkyl, or —CN; $R^4$ can be =O or —OH; R' and R" independently can be H, halogen, substituted or unsubstituted straight or branched chain C1-8 alkyl, substituted or unsubstituted straight or branched chain C1-8 heteroalkyl, substituted or unsubstituted C3-8 cycloalkyl, substituted or unsubstituted C3-8 heterocycloalkyl, or substituted or unsubstituted C5-12 heteroaryl.

In some embodiments, sanguinarine and sanguinarine analogues are alkaloids with fused ring systems, and in some embodiments are benzo[c]phenanthridine alkaloids, having the general structure of Formula (II):

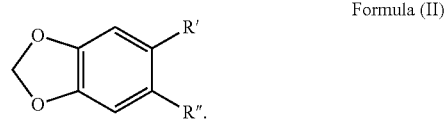

Formula (II)

In compounds of Formula (II), R' and R" are joined in a ring fused to the general core structure. Further, R' and R" represent 1-4 saturated or unsaturated, substituted or unsubstituted fused ring systems fused to the general core structure represented in Formula II, wherein each ring comprises 4-12 atoms, and wherein said atoms of the fused ring systems independently can be carbon, nitrogen, oxygen, silicon, phosporous, or sulfur. Substituent groups can include hydrogen, halogen, substituted or unsubstituted straight or branched chain C1-8 alkyl, substituted or unsubstituted straight or branched chain C1-8 heteroalkyl, substituted or unsubstituted C3-8 cycloalkyl, substituted or unsubstituted C3-8 heterocycloalkyl, =O, —OH, or —CN.

As used herein, the term "attached" signifies a stable covalent bond, certain preferred points of attachment being apparent to those of ordinary skill in the art.

The terms "halogen" or "halo" include fluorine, chlorine, bromine, and iodine. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl (Me), ethyl (Et), propyl (Pr, including n-propyl, isopropyl), butyl (Bu, including n-butyl, t-butyl, isobutyl, sec-butyl), (cyclohexyl)methyl, pentyl, isopentyl, neopentyl, hexyl, heptyl, octyl, nonyl, decyl, undecyl, and the like, including homologs and isomers of, for example, n-pentyl, n-hexyl, n-heptyl, n-octyl, and so forth, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Accordingly, the term "alkyl" can refer to $C_1$-$C_{16}$ straight chain saturated, $C_1$-$C_{16}$ branched saturated, $C_3$-$C_8$ cyclic saturated, $C_3$-$C_8$ cyclic unsaturated, and $C_1$-$C_{16}$ straight chain or branched saturated or unsaturated aliphatic hydrocarbon groups substituted with $C_3$-$C_8$ cyclic saturated or unsaturated aliphatic hydrocarbon groups having the specified number of carbon atoms, and the like. Examples of cyclic alkyl groups include but are not limited to cyclopropyl, cyclobutyl, cyclopentyl, cyclohexyl, cycloheptyl, cyclooctyl, cyclopropylmethyl, and the like.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. The heteroalkyl group can be fully saturated, mono- or polyunsaturated and can include di- and multivalent radicals, having the number of atoms designated. Accordingly, the term "heteroalkyl" can refer to saturated or unsaturated straight or branched chains containing two through 16 atoms along the chain, cyclic saturated or unsaturated groups containing 3-8 atoms in the cycle, and the like. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, —CN, and the like. Up to two heteroatoms may be consecutive, such as, for example, —CH$_2$—NH—OCH$_3$.

The terms "cycloalkyl" and "heterocycloalkyl," by themselves or in combination with other terms, mean, unless otherwise stated, cyclic versions of "alkyl" and "heteroalkyl," respectively. The "cycloalkyl" and "heterocycloalkyl" groups include, for example, monocyclic rings having 3-8 ring members, as well as bicyclic rings having 4-16 ring members, tricyclic rings having 5-24 ring members, and so on. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently, wherein each ring contains between 4-20 atoms, and preferably between 5-10 atoms. A fused ring aryl refers to multiple rings fused together wherein at least one of the fused rings is an aryl ring. The term "heteroaryl" refers to aryl groups (or rings), as defined above, that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Accordingly, the term "aryl" can represent an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e. g. 3-indolyl, 4-imidazolyl). The aryl substituents are independently selected from the group consisting of halo, nitro, cyano, trihalomethyl, $C_{1-16}$alkyl, aryl$C_{1-16}$alkyl, $C_{0-16}$alkyloxy$C_{0-16}$alkyl, aryl$C_{0-16}$alkyloxy$C_{0-16}$alkyl, $C_{0-16}$alkylthio$C_{0-16}$alkyl, aryl$C_{0-16}$alkylthio$C_{0-16}$alkyl, $C_{0-16}$alkylamino$C_{0-10}$alkyl, aryl$C_{0-16}$alkylamino$C_{0-16}$alkyl, di(aryl$C_{1-16}$alkyl)amino$C_{0-16}$alkyl, $C_{1-16}$alkylcarbonyl$C_{0-16}$alkyl, aryl$C_{1-16}$alkylcarbonyl$C_{0-16}$alkyl, $C_{1-16}$alkylcarboxy$C_{0-16}$alkyl, aryl$C_{1-16}$alkylcarboxy$C_{0-16}$alkyl, $C_{1-16}$alkylcarbonylamino$C_{0-16}$alkyl, aryl$C_{1-16}$alkylcarbonylamino$C_{0-16}$alkyl, —$C_{0-16}$alkyl-COOR$_4$, —$C_{0-16}$alkylCONR$_5$R$_6$ wherein R$_4$, R$_5$ and R$_6$ are independently selected from hydrogen, $C_1$-$C_{11}$alkyl, aryl$C_0$-$C_{11}$alkyl, or R$_5$ and R$_6$ are taken together with the nitrogen to which they are attached forming a cyclic system containing 3 to 8 carbon atoms with or without one $C_{1-16}$alkyl, aryl$C_0$-$C_{1-6}$alkyl, or $C_0$-$C_{1-6}$alkylaryl substituent. Aryl includes but is not limited to pyrazolyl and triazolyl.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", R''', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, —COOH, unsubstituted alkyl, unsubstituted heteroalkyl, unsubstituted cycloalkyl, unsubstituted heterocycloalkyl, unsubstituted aryl, and unsubstituted heteroaryl.

The exemplary compounds presently provided are intended to be representative. One of skill in the art will recognize that different compounds from those listed above can be used to achieve a comparable outcome and how to identify such compounds. The fact that Dusp1 gene knockouts are effective in preventing MPN, and do not show negative phenotypes, supports a broad scope of DUSP1 inhibitors that can be used to practice aspects of the present invention.

Compounds that can be screened to determine their utility as TKIs or as Dusp1 inhibitors, include for example, but are not limited to, libraries of known compounds, including natural products, such as plant or animal extracts, synthetic chemicals, biologically active materials including proteins, peptides such as soluble peptides, including but not limited to members of random peptide libraries and combinatorial chemistry derived molecular libraries made of D- or L-configuration amino acids, or both, phosphopeptides (including, but not limited to, members of random or partially degenerate, directed phosphopeptide libraries), antibodies (including, but not limited to, polyclonal, monoclonal, chimeric, human, anti-idiotypic or single chain antibodies, and Fab, F(ab')$_2$ and Fab expression library fragments, and epitope-binding fragments thereof), organic and inorganic molecules, and the like.

In addition to the more traditional sources of test compounds as potential TKIs or as Dusp1 inhibitors, computer modeling and searching technologies permit the rational selection of test compounds by utilizing structural information from the ligand binding sites of relevant proteins. Such rational selection of test compounds can decrease the number of test compounds that must be screened in order to identify a therapeutic compound. Knowledge of the sequences of relevant proteins allows for the generation of models of their binding sites that can be used to screen for potential ligands. This process can be accomplished in several manners known in the art. A preferred approach involves generating a sequence alignment of the protein sequence to a template (derived from the crystal structures or NMR-based model of a similar protein(s), conversion of the amino acid structures and refining the model by molecular mechanics and visual examination. If a strong sequence alignment cannot be obtained then a model can also be generated by building models of the hydrophobic helices. Mutational data that point towards residue-residue contacts can also be used to position the helices relative to each other so that these contacts are achieved. During this process, docking of the known ligands into the binding site cavity within the helices can also be used to help position the helices by developing interactions that would stabilize the binding of the ligand. The model can be completed by refinement using molecular mechanics and loop building using standard homology modeling techniques. (General information regarding modeling can be found in Schoneberg, T. et. al. *Molecular and Cellular Endocrinology* 151:181-93 (1999); Flower, D. *Biochimica et Biophysica Acta* 1422:207-34 (1999); and Sexton, P. *Current Opinion in Drug Discovery and Development* 2:440-8 (1999); specific information regarding screening of compounds which behave similarly to BCI can be found in Molina et al., *Nature Chemical Biology* 2009 5:680-7)

Once the model is completed, it can be used in conjunction with one of several existing computer programs to narrow the number of compounds to be screened by the screening methods of the present invention, like the DOCK program (UCSF Molecular Design Institute, San Francisco, Calif.). In several of its variants it can screen databases of commercial and/or proprietary compounds for steric fit and rough electrostatic complementarity to the binding site. Another program that can be used is FLEXX (Tripos Inc., St. Louis, Mo.).

TKIs and Dusp1 inhibitors for use in the methods described herein also include racemic mixtures, stereoisomers and mixtures of the compounds, including isotopically-labeled and radio-labeled compounds. See e.g., Goding, 1986, MONOCLONAL ANTIBODIES PRINCIPLES AND PRACTICE; Academic Press, p. 104. Such isomers can be isolated by standard resolution techniques, including e.g., fractional crystallization, chiral chromatography, and the like. See e.g., Eliel, E. L. & Wilen S. H., 1993, STEREOCHEMISTRY IN ORGANIC COMPOUNDS; John Wiley & Sons, New York.

In some embodiments, TKIs and Dusp1 inhibitors for use in the methods described herein have asymmetric centers and may occur as racemates, racemic mixtures, and as individual enantiomers or diastereoisomers, with all isomeric forms as well as mixtures thereof being contemplated for use in the compounds and methods described herein. The compounds contemplated for use in the methods described herein do not include those that are known in the art to be too unstable to synthesize and/or isolate.

TKIs and Dusp1 inhibitors for use in the methods described herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds disclosed herein, whether radioactive or not, are encompassed within the contemplated scope.

In some embodiments, metabolites of the TKIs and Dusp1 inhibitors, for use in the methods described herein are useful for the methods disclosed herein.

In some embodiments, the TKIs and Dusp1 inhibitors, for use in the methods described herein are provided in the form of a prodrug. The term "prodrug" refers to a compound that can be converted into a compound (e.g., a biologically active compound) described herein in vivo. Prodrugs can be useful for a variety of reason known in the art, including e.g., ease of administration due e.g., to enhanced bioavailability in oral administration, and the like. The prodrug may also have improved solubility in pharmaceutical compositions over the biologically active compounds. An example, without limitation, of a prodrug is a compound which is administered as an ester (i.e., the "prodrug") to facilitate transmittal across a cell membrane where water solubility is detrimental to mobility but which then is metabolically hydrolyzed to the carboxylic acid, the active entity, once inside the cell where water-solubility is beneficial. Conventional procedures for the selection and preparation of suitable prodrug derivatives are described, for example, in DESIGN OF PRODRUGS, (ed. H. Bundgaard, Elsevier, 1985), which is hereby incorporated herein by reference for the limited purpose describing procedures and preparation of suitable prodrug derivatives.

Accordingly, in some embodiments, the TKIs and Dusp1 inhibitors, for use in the methods described herein are provided in the form of a prodrug ester. The term "prodrug ester" refers to derivatives of the compounds disclosed herein formed by the addition of any of a variety of ester-forming groups, e.g., groups known in the art, that are hydrolyzed under physiological conditions. Examples of prodrug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "Pro-drugs as Novel Delivery Systems", Vol. 14, A.C.S. Symposium Series, American Chemical Society (1975); and BIOREVERSIBLE CARRIERS IN DRUG DESIGN: THEORY AND APPLICATION, edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

In some embodiments, prodrugs can be slowly converted to the compounds described herein useful for the methods described herein when placed in a transdermal patch reservoir with a suitable enzyme or chemical reagent.

Certain TKIs and Dusp1 inhibitors, for use in the methods disclosed herein can exist in unsolvated forms as well as solvated forms, including hydrated forms. In general, the solvated forms are equivalent to unsolvated forms and are encompassed within the scope of contemplated compounds. Certain compounds of the present invention may exist in multiple crystalline or amorphous forms. In general, all physical forms are equivalent for the compounds and methods contemplated herein and are intended to be within the scope disclosed herein.

Administration

Particular aspects of the invention relate to the use of TKIs and Dusp1 inhibitors, and/or their physiologically acceptable salts or esters, for the preparation of a medicament (pharmaceutical preparation), in particular by nonchemical methods. They can be converted here into a suitable dosage form together with at least one solid, liquid and/or semiliquid excipient or assistant and, if desired, in combination with one or more further active ingredients.

Particular aspects of the invention furthermore relate to medicaments comprising at least one TKI, such as a Dusp1 inhibitor, and/or its pharmaceutically usable derivatives, solvates and stereoisomers, including mixtures thereof in all ratios, and optionally excipients and/or assistants.

According to particular aspects, the therapeutic compounds and compositions, including TKIs and Dusp1 inhibitors for use in the methods described herein, can be administered by any conventional method available for use in conjunction with pharmaceutical drugs, either as individual therapeutic agents or in a combination of therapeutic agents. Such therapeutics can be administered by any pharmaceutically acceptable carrier, including, for example, any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional medium or agent is incompatible with the active compound, such media can be used in the compositions of the invention. Supplementary active compounds can also be incorporated into the compositions. A pharmaceutical composition in particular aspects of the invention is formulated to be compatible with its intended route of administration. Routes of administration include for example, but are not limited to, intravenous, intramuscular, and oral, and the like. Additional routes of administration include, for example, sublingual, buccal, parenteral (including, for example, subcutaneous, intramuscular, intraarterial, intradermal, intraperitoneal, intracisternal, intravesical, intrathecal, or intravenous), transdermal, oral, transmucosal, and rectal administration, and the like.

Solutions or suspensions used for appropriate routes of administration, including, for example, but not limited to parenteral, intradermal, or subcutaneous application, and the like, can include, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose, and the like. The pH can be adjusted with acids or bases, such as, for example, hydrochloric acid or sodium hydroxide, and the like. The parenteral preparation can be enclosed in, for example, ampules, disposable syringes, or multiple dose vials made of glass or plastic, and the like.

Exemplary pharmaceutical compositions suitable for injectable use include, for example, sterile aqueous solutions (where water soluble) or dispersions and sterile powders for the extemporaneous preparation of sterile injectable solutions or dispersion, and the like. For intravenous administration, suitable carriers include, for example, physiological saline, bacteriostatic water, Cremophor ELTM (BASF, Parsippany, N.J.) or phosphate buffered saline (PBS), and the like. In all cases, the composition should be fluid to the extent that easy syringability exists. The carrier can be a solvent or dispersion medium containing, for example, water, ethanol, polyol (for example, glycerol, propylene glycol, and liquid polyethylene glycol, and the like), and suitable mixtures thereof, and the like. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, such as, for example, parabens, chlorobutanol, phenol, ascorbic acid, thimerosal, and the like. In many cases, it can be preferable to include isotonic agents, such as, for example, sugars, polyalcohols such as mannitol, sorbitol, and sodium chloride, and the like, in the composition. Prolonged absorption of the injectable compositions can be brought about by including in the composition an agent which delays absorption such as, for example, aluminum monostearate and gelatin, and the like.

Exemplary sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Exemplary oral compositions generally include an inert diluent or an edible carrier. They can be enclosed in gelatin capsules or compressed into tablets, for example. For oral administration, the agent can be contained in enteric forms to survive the stomach or further coated or mixed to be released in a particular region of the gastrointestinal (GI) tract by known methods. For the purpose of oral therapeutic administration, the active compound can be incorporated with excipients and used in the form of tablets, troches, or capsules, or the like. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches, and the like can contain any of the following exemplary ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate; a glidant such as colloidal silicon dioxide; a sweetening agent such as sucrose or saccharin; or a flavoring agent such as peppermint, methyl salicylate, or orange flavoring, or the like. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatin, carbohydrates, such as lactose or starch, magnesium stearate, talc or VASELINE®. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilized and the resultant lyophilizates used, for example, to prepare injection preparations. The preparations indicated may be sterilized and/or comprise assistants, such as lubricants, preservatives, stabilizers and/or wetting agents, emulsifying agents, salts for modifying the osmotic pressure, buffer substances, colorants and flavors and/or a plurality of further active ingredients, for example one or more vitamins.

For administration by inhalation, the compositions can be delivered in the form of an aerosol spray from pressured container or dispenser, which contains a suitable propellant, e.g., a gas such as carbon dioxide, or a nebulizer, or the like. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives, and the like. Transmucosal administration can be accomplished through the use of nasal sprays or suppositories. For transdermal administration, the active compounds are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In particular embodiments, the active TKIs and/or Dusp1 inhibitors are prepared with carriers that will protect the compound against rapid elimination from the body, such as a controlled release formulation, including implants and microencapsulated delivery systems, and the like. Biodegradable, biocompatible polymers can be used, such as, for example, ethylene vinyl acetate, polyanhydrides, polyglycolic acid, collagen, polyorthoesters, and polylactic acid, and the like. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference in its entirety.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The details for the dosage unit forms of the invention are dictated by and directly dependent on the unique characteristics of the active compound and the particular therapeutic effect to be achieved, and the limitations inherent in the art of compounding such an active compound for the treatment of individuals. Such details are known to those of skill in the art.

The dosage administered will, of course, vary depending upon known factors, such as the pharmacodynamic characteristics of the particular agent and its mode and route of administration; the age, health, sex, weight, and diet of the recipient; the nature and extent of the symptoms; the kind of concurrent treatment; the time and frequency of treatment; the excretion rate; and the effect desired. A daily dosage of active ingredient can be expected to be about 0.001 to 1000 milligrams (mg) per kilogram (kg) of body weight, with the preferred dose being 0.01 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

In some embodiments, the TKIs and/or Dusp1 inhibitors, for use in the methods described herein exhibit inhibitory activity against a tyrosine kinase, such as Dusp1, with activities≥1 µM, e.g., about 1, 2, 3, 4, 5, 6, 7, 8, 9, 10, 11, 12, 13, 14, 16, 18, 20, 22, 24, 26, 28, 30, 32, 34, 36, 38, 40, 45, 50, 55, 60, 65, 70, 75, 80, 85, 90, 95, 100 µM, or even greater. In some embodiments, the compounds exhibit inhibitory activity against a tyrosine kinase, such as Dusp1, with activities between 0.1 µM and 1 µM, e.g., about 0.1, 0.2, 0.3, 0.4, 0.5, 0.6, 0.7, 0.8, 0.9 or 1.0 µM. In some embodiments, compounds described herein exhibit inhibitory activity against a tyrosine kinase, such as Dusp1, with activities≤0.1 µM, e.g., about 1, 2, 5, 10, 15, 20, 30, 40, 50, 60, 70, 80, 90, or 100 nM. Ranges of values using a combination of any of the values recited herein as upper and/or lower limits are also contemplated, for example, but not limited to, 1-10 nM, 10-100 nM, 0.1-1 µM, 1-10 µM, 10-100 µM, 100-200 µM, 200-500 µM, or even 500-1000 µM. In some embodiments, the inhibitory activity is in the range of about 1-10 nM, 10-100 nM, 0.1-1 µM, 1-10 µM, 10-100 µM, 100-200 µM, 200-500 µM, or even 500-1000 µM. It is understood that for purposes of quantification, the terms "activity," "inhibitory activity," "biological activity," "tyrosine kinase", "Dusp1 activity" and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

In some embodiments, a dose or a therapeutically effective dose of a compound for use in the methods described herein will be that which is sufficient to achieve a plasma concentration of the compound or its active metabolite(s) within a range set forth herein, e.g., about 1-10 nM, 10-100 nM, 0.1-1 µM, 1-10 µM, 10-100 µM, 100-200 µM, 200-500 µM, or even 500-1000 µM, preferably about 1-10 nM, 10-100 nM, or 0.1-1 µM. Without wishing to be bound by any theory, it is believed that such compounds are indicated in the treatment or management of MPNs.

In some embodiments, the compounds persist in the blood plasma after intravenous infusion. In some embodiments, greater than 50% of the initial compound concentration persists in the blood plasma of mice 1 hour after intravenous injection. In some embodiments, greater than 50% of the initial compound concentration persists in the blood plasma of mice 3 hours or longer after intravenous injection.

The invention also relates to a set (kit) consisting of separate packs of: an effective amount of one or more TKIs and/or Dusp1 inhibitors, and/or its pharmaceutically usable derivatives, solvates and stereoisomers, including mixtures thereof in all ratios, and an effective amount of a further medicament active ingredient. At least one inactive ingredient may optionally be included in the kit, as set forth above.

The set comprises suitable containers, such as boxes, individual bottles, bags or ampoules. The set may, for example, comprise separate ampoules each containing an effective amount of one or more TKIs and/or Dusp1 inhibitors, and/or its pharmaceutically usable derivatives, solvates and stereoisomers, including mixtures thereof in all ratios, and an effective amount of a further medicament active ingredient in dissolved or lyophilized form.

The invention furthermore relates to the use of one or more TKIs and/or Dusp1 inhibitors, and/or their pharmaceutically usable derivatives, solvates and stereoisomers, including mixtures thereof in all ratios, for the preparation of a medicament for the treatment of MPN, in combination with at least one further active ingredient. At least one inactive ingredient may optionally be included in the medicament, as set forth above.

Having described the invention in detail, it will be apparent that modifications, variations, and equivalent embodiments are possible without departing from the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

CML was Used as a Disease Paradigm

The mechanism of TKI efficacy has been described in chronic myeloid leukemia (CML) as a model system, as shown in FIG. 2. This figure describes the mechanism of oncogene-addiction where Fos and Dusp1 mediate dependence to BCR-ABL. The level of expression of both Fos and Dusp1 determines the TKI efficacy: higher Fos and Dusp1 expression cause resistance, while lower expression sensitizes the leukemic cells to TKI.

Example 2

Expression of c-Fos, Dusp1 and Zfp36 were Demonstrated to Constitute a Common Signature in Imatinib Resistant Cells Both in Mice and Men Therapeutic response to TKI is mediated by oncogene-addiction to mutant tyrosine kinase oncoproteins.[10-12] However, the mechanism of oncogene addiction is not well understood, nor is how cancer cells that do not respond to TKI therapy (MRD) escape addiction from the driver oncogene. In addition, recent studies have revealed that growth factor signaling mediates resistance to TKI therapy in both leukemia and solid organ tumors.[18-20] However, it remains to be determined if intrinsic resistance conferred by a diverse set of growth factors utilizes distinct or a shared molecular pathway.

To understand how growth factor signaling induces TKI resistance, growth factor-induced mitigation of TKI response in the interleukin-3 (IL-3)-dependent BaF3 cell line was modeled; results are shown in FIG. 3: (A) Immunoblots showing conditional expression of BCR/ABL by doxycycline in BaF3-LTBA cells. Note the absence of basal expression of BCR/ABL. (B) Bar graph illustrating percent survival of BaF3-LTBA cells treated with imatinib+/−IL3. (C) Bar graph illustrating percent survival of BaF3-BCR/ABL cells (constitutive expression of BCR/ABL) treated with imatinib+/−IL3. (D) Immunoblots showing equal inhibition of BCR/ABL in BaF3-BCR/ABL cells by imatinib+/−IL3. (E) Bar graph illustrating percent survival of K562 cells (An erythromyeloblastoid leukemia cell line derived from a blast crisis CML patient) treated with imatinib+/−cytokines (as indicated). (F) Venn diagram of differentially expressed genes between three experiments. 1) BaF3-LTBA cells and/or BaF3-BCR/ABL treated with imatinib+/−IL3, 2) K562 treated with imatinib+/−erythropoietin, and 3) primary CML patients before and after two weeks of imatinib treatment. (G) Real-time qPCR analysis shows BCR/ABL induced expression of c-Fos, Dusp1 and Zfp36+/−IL3. (H) Immunoblot showing induction of c-Fos, Dusp1 and Zfp36 by BCR/ABL+/−IL3. (I) Bar graph representing densitometric quantification of total Fos, phospho-Fos, Dusp1 and Zfp36 from the above described protein blots. (J) Real-time qPCR analysis illustrating expression of c-FOS, DUSP1, and ZFP36 in primary CML patient peripheral blood mononuclear cells normalized to CD34+ cells from normal volunteers (black bar). Four chronic phase (CP) and three blast crisis (BC) patients were analyzed.

Figure 3A:
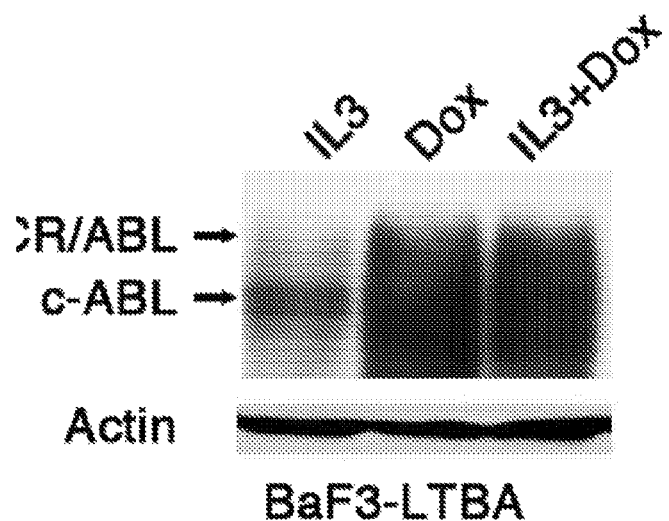
FIG. 3 shows that expression of c-Fos, Dusp1 and Zfp36 constitute a common signature in imatinib resistant cells both in mice and men.
Figure 3B:
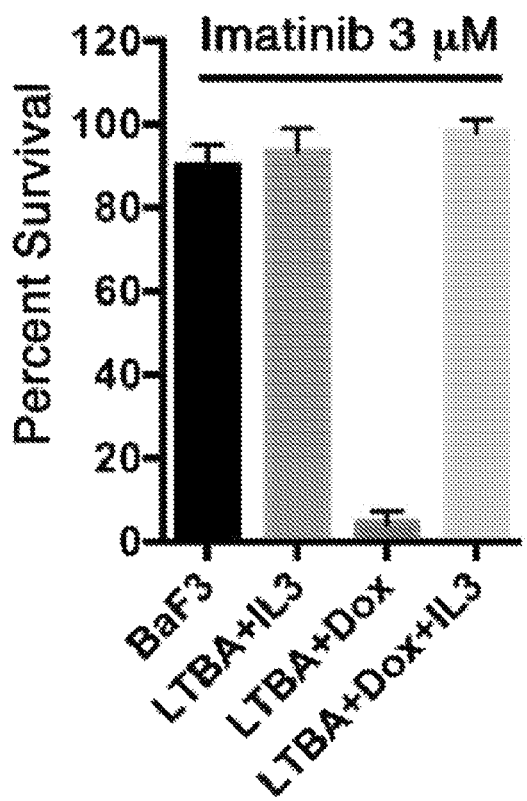
Figure 3C:
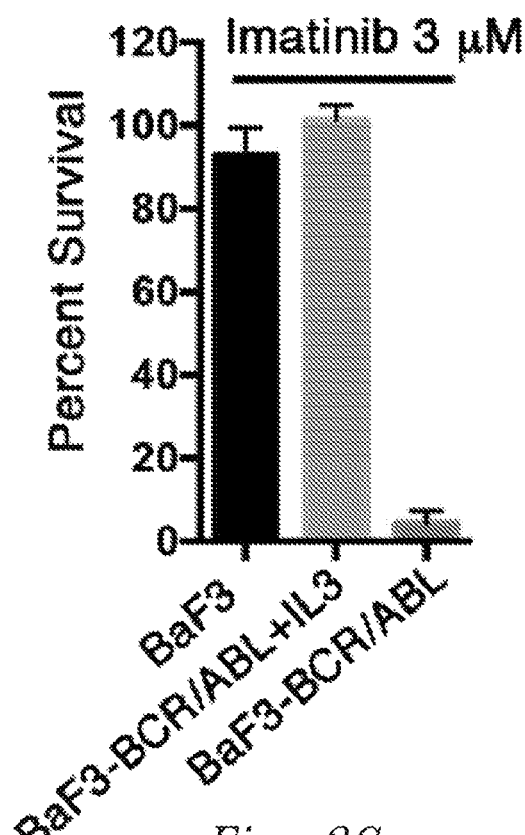
Figure 3D:
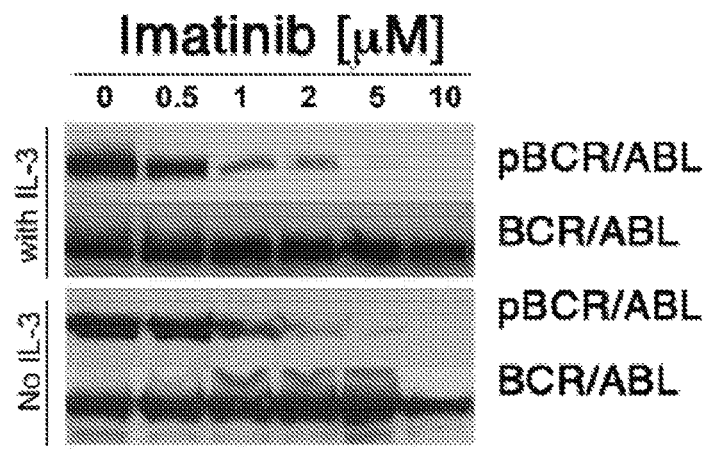
Figure 3E:
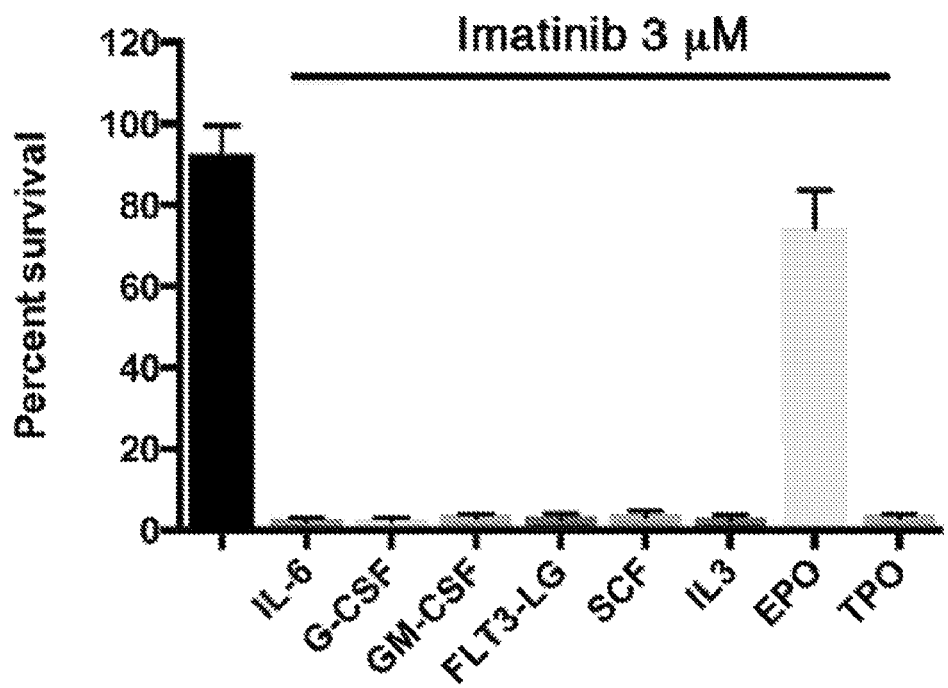
Figure 3J:
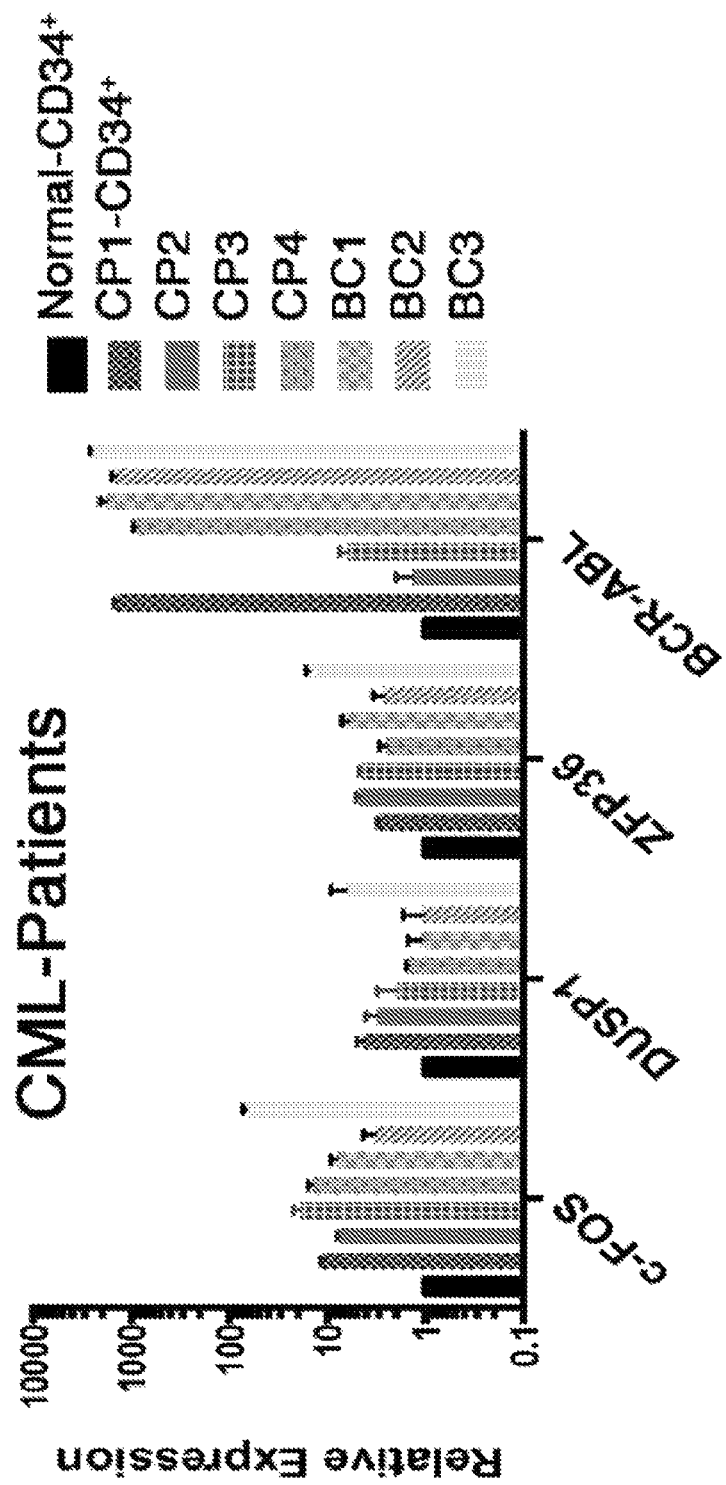

BaF3 cells were generated with tetracycline-inducible expression of BCR/ABL (BaF3-LTBA, FIG. 3A), as well as those with constitutive BCR/ABL expression (BAF3-BCR/ABL, FIG. 3B). Imatinib treatment of both BCR/ABL-induced BaF3-LTBA as well as BAF3-BCR/ABL cells causes cell death, while addition of IL3 confers resistance to TKI even during sustained inhibition of BCR/ABL enzymatic activity (FIG. 3B-D). Likewise, erythropoietin conferred imatinib resistance in the human CML cell line K562 (FIG. 3E). Thus, growth factor induced resistance to imatinib can be recapitulated in vitro.

Applicant hypothesized that the critical genes mediating TKI resistance might be directly modulated by both BCR/ABL and growth factor signaling. Therefore, the expression profiles of BCR/ABL-induced BaF3-LTBA with and without IL3 (192 genes) were compared, as well as imatinib-treated BAF3-BCR/ABL cells with and without IL3 (308 genes). Next, erythropoietin-modulated gene expression was evaluated in imatinib-treated K562 cells (1338 genes). Finally, existing gene expression profiles were analyzed from primary-CML-patient bone-marrow CD34+ cells collected before and after two weeks of imatinib treatment.[61] When the three data sets above are compared, only three genes are commonly expressed between all comparisons (c-Fos, Dusp1 and Zfp36; FIG. 3F). Given that this analysis includes both constitutive and inducible expression of BCR/ABL, as well as imatinib treatment of BCR/ABL expressing cells, these genes are likely proximal to BCR/ABL signaling and thus more likely to also be modulated by growth factors. Indeed, expression analysis of these genes in BaF3-BCR/ABL cells and CML patient samples revealed that c-Fos, Dusp1 and Zfp36 are induced by BCR/ABL and growth factor signaling (FIG. 3G-J). Similar to IL3, ectopic overexpression of c-Fos, Dusp1, and Zfp36 by retroviral vectors in BaF3-BCR/ABL cells impaired imatinib response (data not shown). These results suggest that c-Fos, Dusp1, and Zfp36 are functional mediators of growth factor-induced imatinib resistance.

Conversely, depletion of c-Fos, Dusp1 and Zfp36 (alone or in combination) by shRNA mediated knockdown reduced BCR/ABL-dependent proliferation and survival, while parental BaF3 cells were not affected (data not shown). These results indicate that c-Fos, Dusp1 and Zfp36 are critically required for BCR/ABL dependent survival. Reduced expression of c-Fos and Dusp1 alone or together sensitized BCRABL expressing cells to imatinib, even in the presence of IL3. However, depletion of Zfp36 sensitized both parental BaF3 and BaF3-BCR/ABL cells to imatinib, suggesting that (unlike, c-Fos and Dusp1) Zfp36 is not differentially required by BCR/ABL-expressing cells. Therefore, subsequent analyses focused upon c-Fos and Dusp1.

Example 3

Figure 4C:
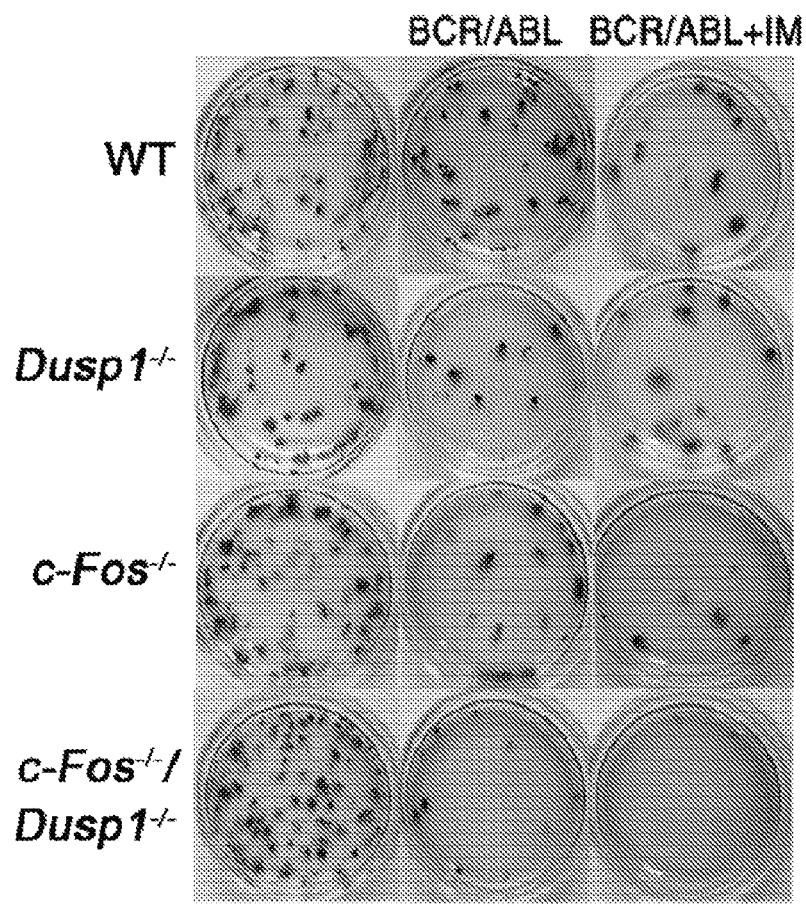
FIG. 4 shows that genetic deletion of c-Fos and Dusp1 significantly increases imatinib response in BCR/ABL-induced leukemia.
Figure 4D:
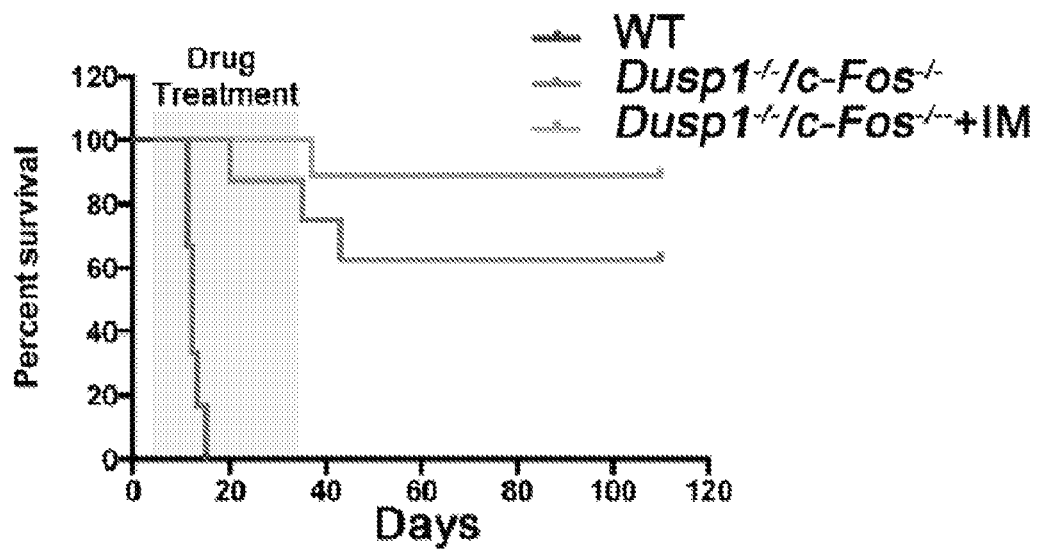
Figure 4E:
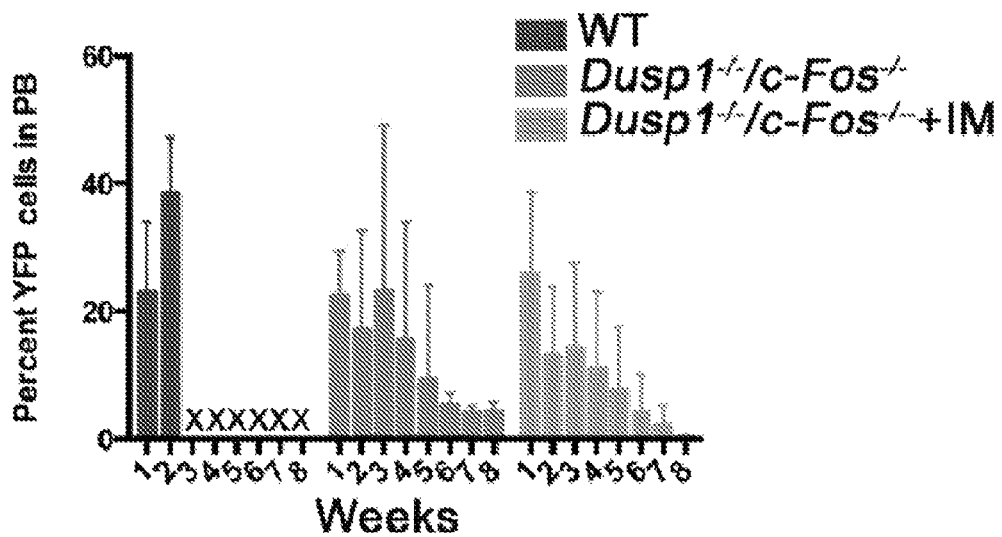

Genetic Deletion of c-Fos and Dusp1 Significantly Increased Imatinib Response in BCR/ABL Induced Leukemia To determine the role of c-Fos and Dusp1 in CML development mice lacking Dusp1$^{-/-}$ [62], c-Fos$^{fl/fl}$ [63] (ROSACre$^{ERT2}$c-Fos$^{fl/fl}$) and both genes (ROSACre$^{ERT2}$c-Fos$^{fl/fl}$Dusp1$^{-/-}$) were analyzed; results are shown in FIG. 4: (A) Schematic representation of in vitro and in vivo experiments to analyze BCR/ABL disease using Dusp1$^{-/-}$, ROSACre$^{ERT2}$c-Fos$^{fl/fl}$ and ROSACre$^{ERT2}$c-Fos$^{fl/fl}$Dusp1$^{-/-}$ mice. Kit$^+$ cells from mouse bone marrow were transduced with BCR/ABL-IRES-YFP retroviruses. Five thousand GFP$^+$ cells were plated for in vitro CFU assays, and 40,000 YFP$^+$ cells were transplanted for in vivo leukemia development in lethally irradiated C57Bl6 mice. (B) Percent CFU derived from Kit$^+$ cells expressing BCR/ABL in the, and c-Fos/Dusp1. (C) Representative plates showing BCR/ABL positive colonies from wild type (WT)), Dusp1$^{-/-}$, ROSACre$^{ERT2}$c-Fos$^{fl/fl}$ and ROSACre$^{ERT2}$c-Fos$^{fl/fl}$Dusp1$^{-/-}$ mice. Note that imatinib treatment completely suppressed the emergence of CFU from Fos$^{-/-}$ Dusp1$^{-/-}$ cells. (D) Survival curves of mice transplanted with BCR/ABL-YFP transduced Kit+ cells from and ROSACre$^{ERT2}$c-Fos$^{fl/fl}$-Dusp1$^{-/-}$ mice. Data shown are from two independent transplant experiments (n p=0.017). Below, Bar graphs illustrating leukemic burden in mice transplanted with BCR-ABL Kit$^+$ cells, measured by the level of YFP in peripheral blood as a surrogate for BCR/ABL expression. Cohorts of mice that died are represented as X. Note mice surviving in c-Fos$^{-/-}$ Dusp1$^{-/-}$ transplants lack YFP+ cells in blood and marrow after seven weeks.

Hematopoietic stem-cell-enriched populations (LSK; Lin$^-$, Sca1$^+$ and Kit$^+$) were used for in vitro CFU assays and Kit$^+$ cells transduced with BCR/ABL-IRES-YFP retroviruses for in vivo CML development (FIG. 4A). Genetic deletion of c-Fos or Dusp1 significantly reduced (50%) CFU from BCR/ABL-LSK cells, while control cells (YFP positive LSK cells transduced with MSCV-Ires-YFP viruses) were not affected (FIG. 3C). Strikingly, loss of both c-Fos and Dusp1, suppressed (~90%) BCR/ABL dependent CFU, and treatment with imatinib completely eradicated BCR/ABL positive colonies (FIGS. 3B and C).

For in vivo analysis, mice were transplanted with 40 thousand bone marrow Kit$^+$ cells expressing BCR/ABL and YFP. Recipient mice developed fatal leukemia with a disease latency of 2-3 weeks.[64] While deletion of Dusp1 delayed BCR/ABL induced leukemia by one week, imatinib treatment did not show significant reduction in leukemic burden, and all mice died within 3-4 weeks (data not shown). In contrast, deletion of c-Fos alone showed a greater disease latency (7-8 weeks). Surprisingly, one-month imatinib treatment of these mice showed significant reduction in leukemic burden (0.5-4%) and saved ~50% of mice from leukemic death. Importantly, discontinuing treatment did not result in disease relapse, suggesting the elimination of TKI-resistant MRD. In control experiments where c-Fos was not deleted by tamoxifen, the recipients showed similar kinetics of disease latency as WT mice (data not presented).

Interestingly, deletion of both c-Fos and Dusp1 saved ~60% of the mice from leukemic death with significantly reduced leukemic burden (ROSACre$^{ERT2}$c-Fos$^{fl/fl}$Dusp1$^{-/-}$: FIG. 4D). Control ROSACre$^{ERT2}$c-Fos$^{fl/fl}$Dusp1$^{-/-}$ mice showed modestly prolonged survival, which was correlated to lower c-Fos mRNA expression in these mice (data not presented). Nevertheless, complete deletion of both c-Fos and Dusp1 combined with a five-week imatinib treatment eradicated all leukemic cells from peripheral blood and bone marrow (FIG. 4D). Again, discontinuing treatment did not result in disease relapse, as measured by YFP positive cells in blood and bone marrow at the end of experiment (four months). Thus, genetic deletion of c-Fos and Dusp1 sensitizes BCR/ABL expressing cells (but not wild type cells) to imatinib treatment and eliminates TKI-resistant MRD.

To rule out potential non-specific effects of c-Fos or Dusp1 gene targeting on BCR/ABL induced leukemia, two experiments were performed; results are shown in FIG. 5: (A) Primary structure of c-Fos and its dominant negative version, c-Fos-DRK, lacking the DNA binding domain. (B) Tertiary structure of c-Fos bound with DNA, showing the homo/heterodimer assembly of c-Fos, and how DNA binding domains are assembled to bind its cognate binding site (PDB: 1FOS). (C) Percent CFU from BCR/ABL-YFP$^+$ wild-type (WT) Kit$^+$ cells expressing dominant negative c-Fos-DRK+/−imatinib, compared to BCR/ABL-YFP$^+$ Fos$^{-/-}$ Kit$^+$ cells+/−imatinib. Dominant negative c-Fos and Fos$^{-/-}$ equivalently impair CFU response to imatinib. (D) Percent CFU from c-Fos$^{-/-}$Dusp1$^{-/-}$ Kit$^+$ cells with retroviral-vector-mediated rescue of Fos and Dusp1 expression. Expression of c-Fos-wild type (WT) partially rescued the phenotype, while expression of both Dusp1 and c-Fos using a mono-cistronic vector (P2A peptide cleavage) restored CFU numbers to normal levels. Data shown are from two independent experiments±S.D (n=3).

First, a dominant negative c-Fos (lacking the DNA binding domain, FIGS. 5A and B) with BCR/ABL in wild-type (WT-C57Bl/6) bone marrow cells was expressed. Expression of this c-Fos dominant negative resulted in a phenotype similar to c-Fos deletion; >50% reduction in BCR/ABL dependent CFUs (FIG. 5C). Second, expression of wild type c-Fos and Dusp1 in c-Fos$^{-/-}$ Dusp1$^{-/-}$ cells rescued BCR/ABL-dependent CFU development (FIG. 5D). While these experiments provide clear evidence that both c-Fos and Dusp1 as critical regulators of BCR/ABL-induced transformation and leukemia development, they are not critically required for hematopoiesis. Specifically, ROSACre$^{ERT2}$c-Fos$^{fl/fl}$Dusp1$^{-/-}$ injected with tamoxifen and observed for six months were healthy and did not show apparent defects (data not shown).

Together, these data indicate that genetic loss of both c-Fos and Dusp1 has synthetic lethality to BCR/ABL, suggesting that they are excellent potential drug targets.

Example 4

Chemical Inhibition of c-Fos, Dusp1 and BCR/ABL Eradicated Minimal Residual Disease (MRD)

Figure 5A:
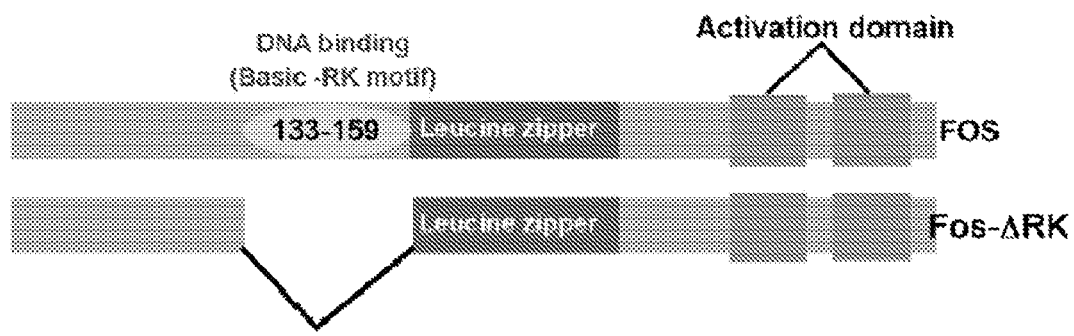
FIG. 5 shows that ectopic expression of Fos and Dusp1 rescued the synthetic lethality induced by BCR-ABL expression.
Figure 5B:
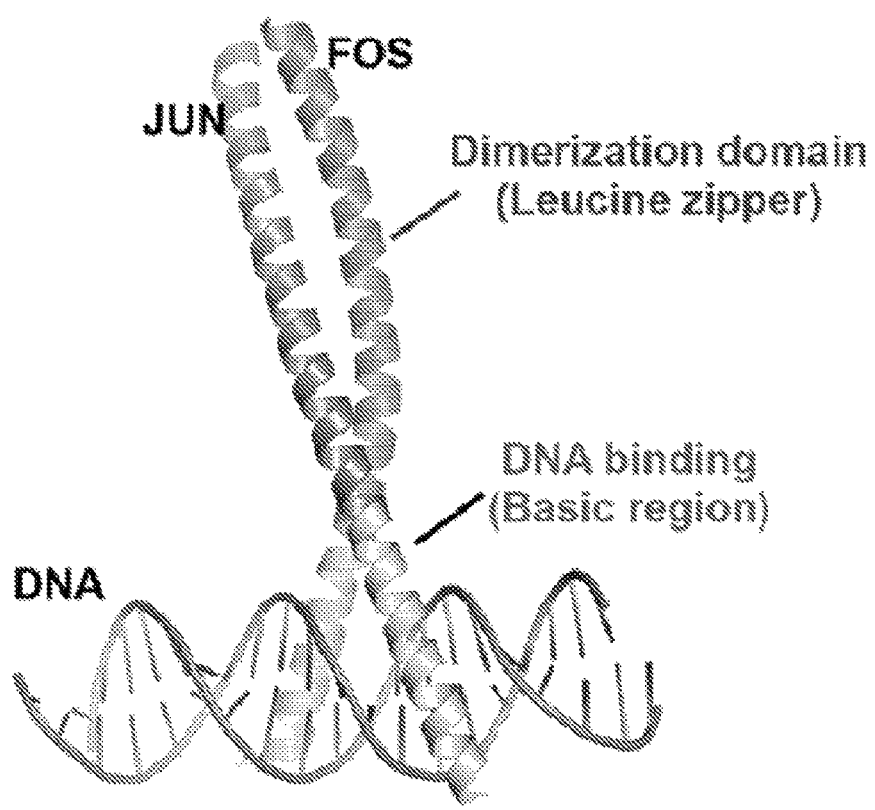
Figure 5C:
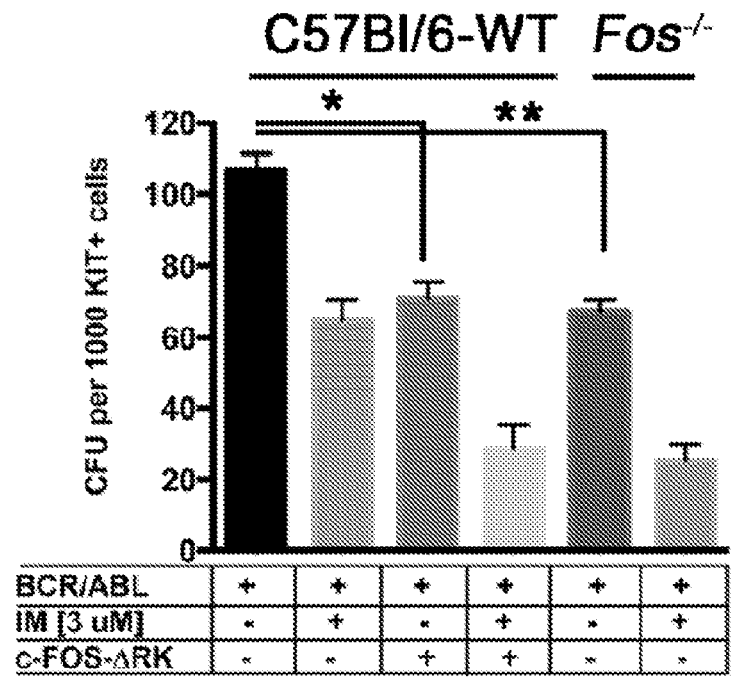
Figure 5D:
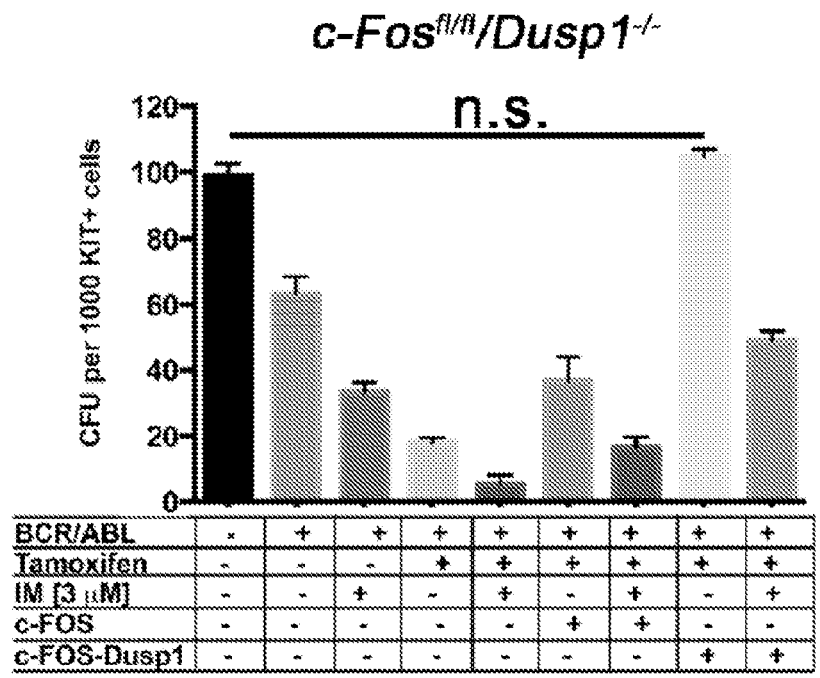

To test c-Fos and Dusp1 as potential drug targets, in vitro and in vivo experiments were performed using small molecule inhibitors of c-Fos and Dusp1 (FIG. 5A). CFU analysis of BCR/ABL-LSK cells treated with c-Fos and Dusp1 inhibitors recapitulated the genetic data; results are shown in FIG. 6: (A) Schematic for small molecule inhibitors of c-Fos (difluorocurcumin; DFC) and Dusp 1 ((E)-2-benzylidene-3-(cyclohexylamino)-2,3-dihydro-1H-inden-1-one; BCI) in vitro and in vivo analysis in CML. (B) Percent CFU from normal and BCR/ABL LSK cells (Lin$^-$Sca1$^+$Kit$^+$), with c-Fos inhibitor (DFC), Dusp1 inhibitor (BCI)+/−imatinib. Representative data shown are the mean colony number from two independent experiments±S.D. (*=p<0.01, **=p<0.002). (C) Survival curve of BCR/ABL-expressing Kit$^+$ cell recipients treated with vehicle (blue), imatinib (red), and a combination of imatinib with DFC and BCI (green). Data shown are from two independent transplant experiments (n=12; p=0.0285). Note that Imatinib+DFC+BCI treatment discontinuation at day 35 did not result in relapse; suggesting complete eradication of MRD. (D) Percent of YFP$^+$ cells in peripheral blood of mice treated with imatinib or Imatinib+DFC+BCI.

Figure 6A:
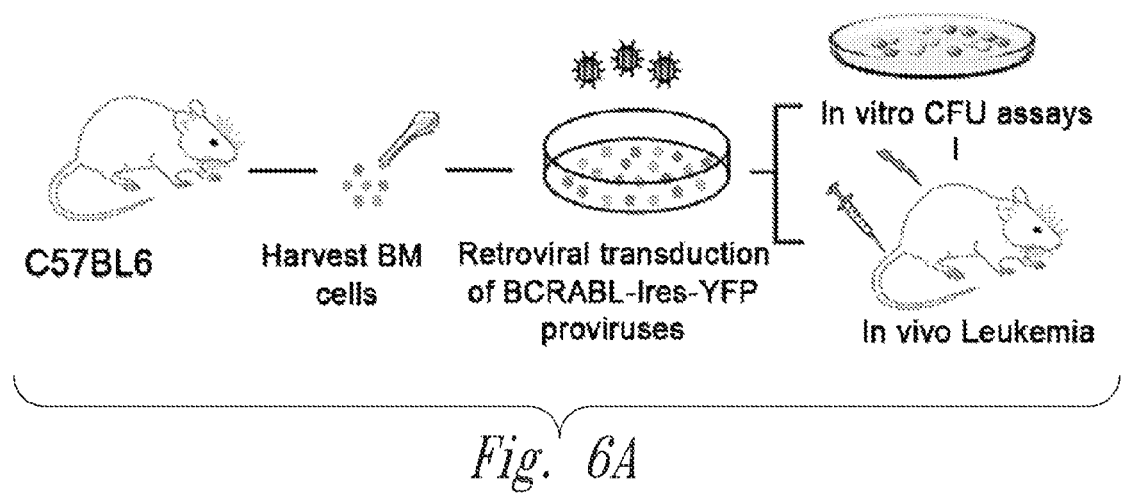
FIG. 6 shows that chemical inhibition of c-Fos, Dusp1 and BCR/ABL eradicates minimal residual disease (MRD).
Figure 6B:
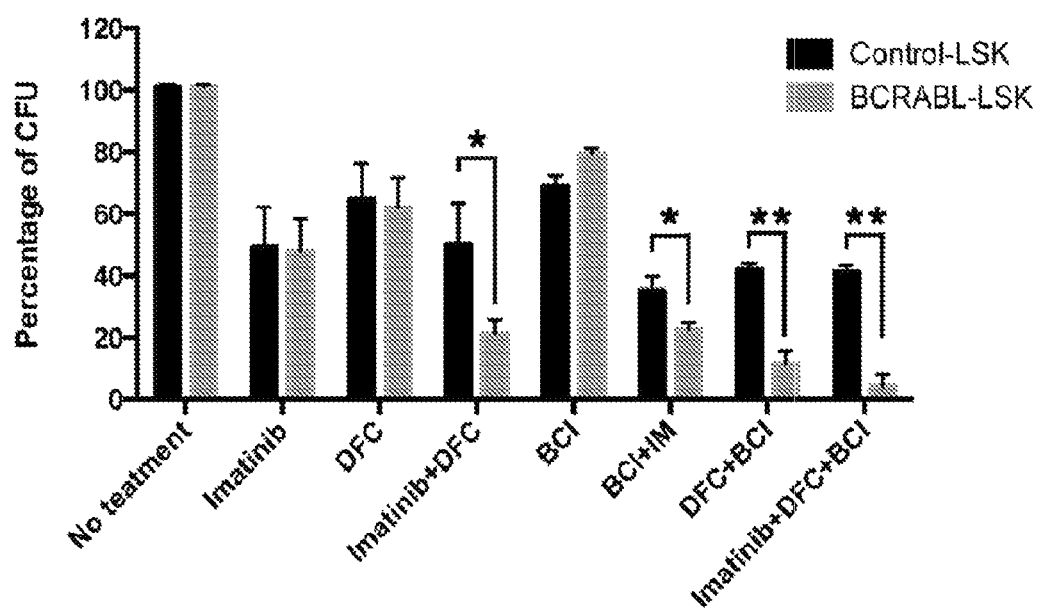

Specifically, a combination of BCI (Dusp1 inhibitor[65], DFC (Fos inhibitor[66]), and imatinib (BCR/ABL inhibitor) completely suppressed CFU formation (Imatinib+DFC+BCI; FIG. 6B). In order to avoid drug-mediated off-target effects on leukemic CFU, two other chemically distinct compounds targeting c-Fos; curcumin[67] and NDGA[68] and DFC[66]. A comparative analysis of these inhibitors revealed that both curcumin NDGA and DFC (Imatinib+NDGA+BCI and Imatinib+curcumin+BCI) are effective in suppressing BCR/ABL-positive CFU formation. The effects of these compounds are unlikely to be non-specific given that all three compounds gave similar results.

Figure 6C:
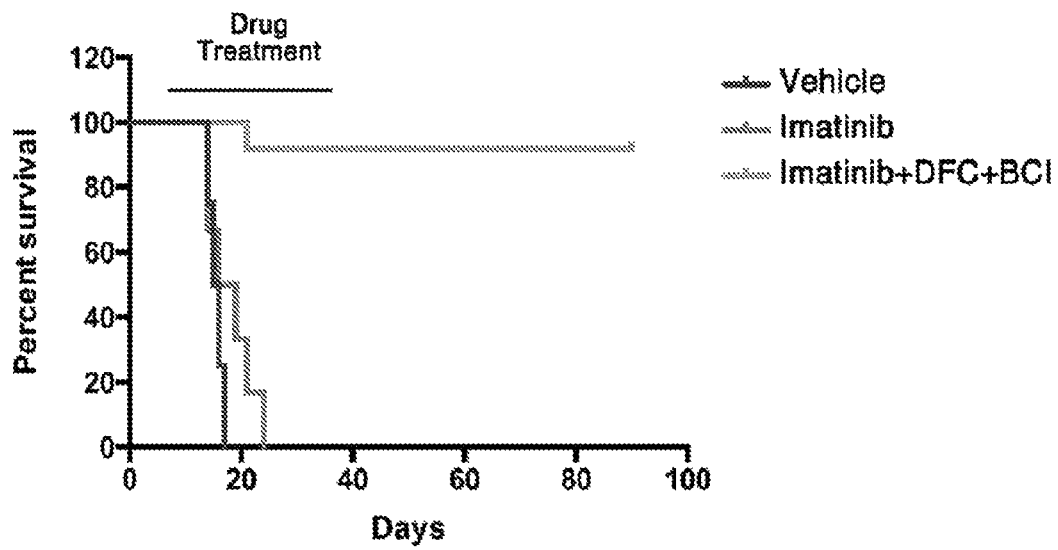
Figure 6D:
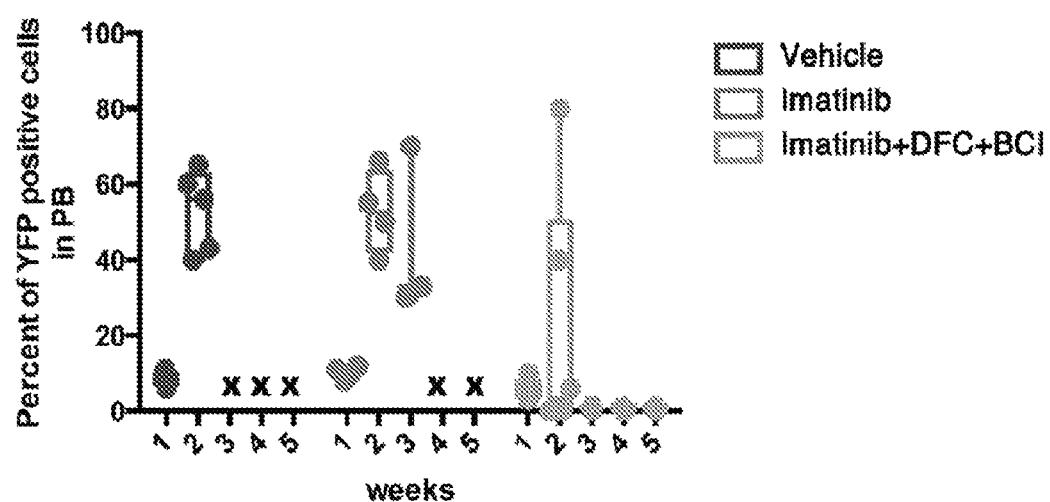

Next, in vivo efficacy was examined using a retroviral bone marrow transduction transplantation CML model. A one month treatment with Imatinib+DFC+BCI saved ~90 percent of mice, and MRD was not detected by flow cytometry (FIGS. 6C and D). Imatinib+curcumin+BCI, and Imatinib+NDGA+BCI saved 50 and 60% of the recipient mice, respectively. By comparison, one-month treatment with individual compounds+/−imatinib was less effective in treating CML disease.

Together, these results indicate that Imatinib+DFC+BCI is more efficient at targeting MRD/leukemic stem cells, perhaps due to superior DFC pharmacokinetics.[66,69]

Example 5

Genetic Evaluation of Dusp1 Expression in Mouse Models of MPD was Performed

Imatinib treatment in CML is not curative because LICs and almost all patients invariably relapse when treatment is discontinued. It has been shown that c-Fos and Dusp1 confer resistance to TKI, and that targeting these proteins by small molecule inhibitors cured CML mice. Based on these observations, it was reasoned that TKI refractoriness in JAK2 targeted MPD might be due to elevated expression of either c-Fos and Dusp1.

Figures 7A, 7B:
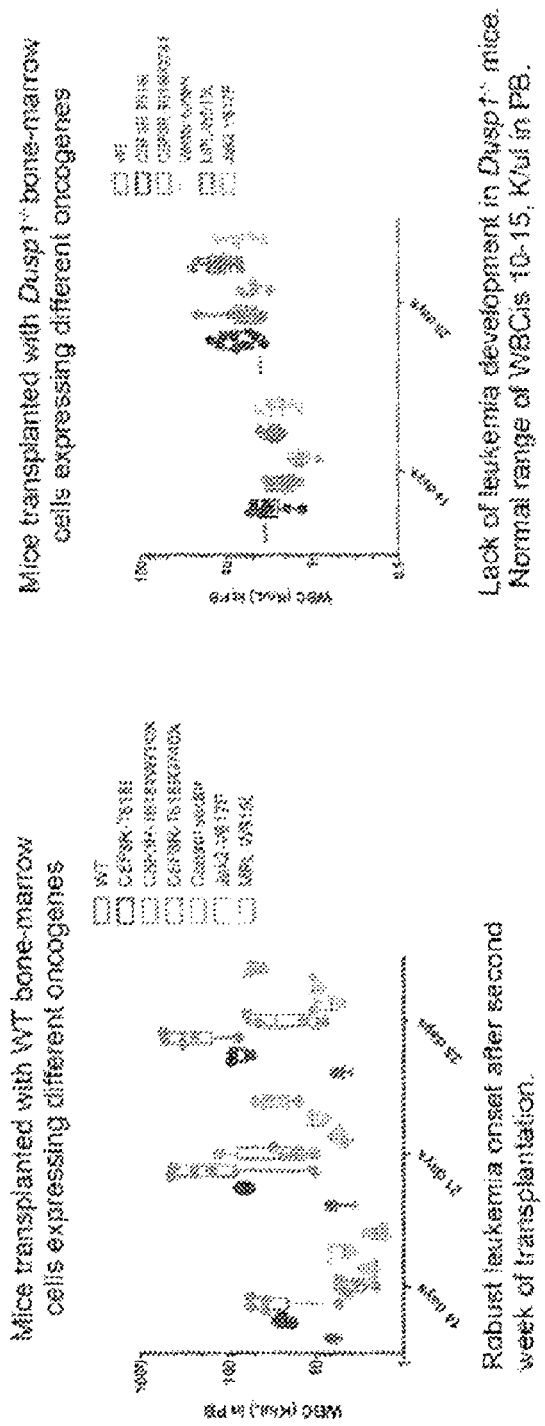
FIG. 7 shows results from transplanting mice with bone marrow cells expressing different oncogenes.
Figure 8:
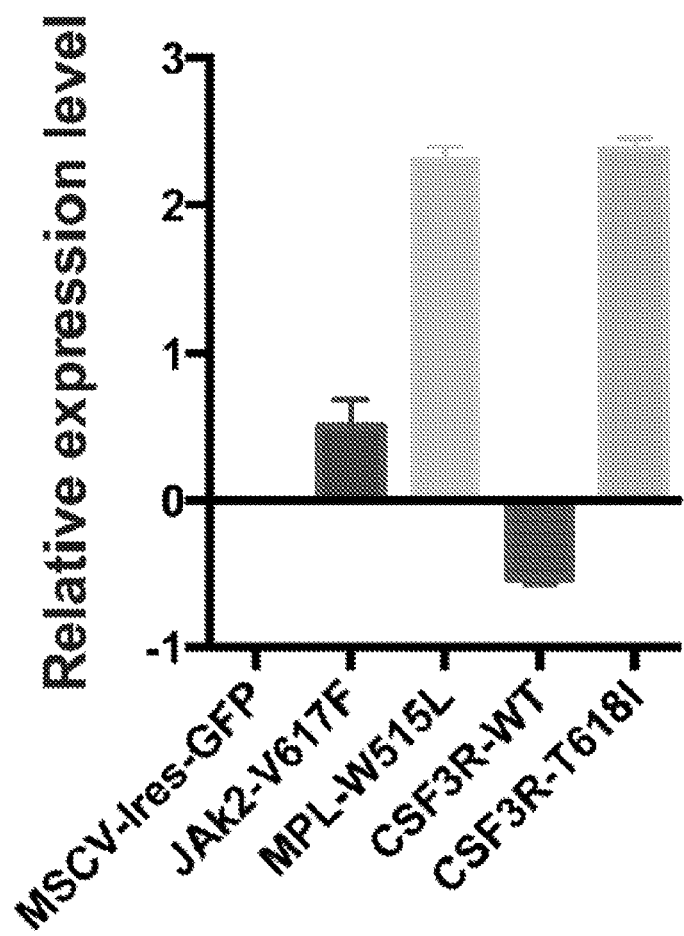
FIG. 8 shows induction of Dusp1 in MPD cells. Bar graph showing q-PCR analysis of Dusp1 in $Kit^+$ cells expressing Jak2-V617F, CSF3RWT, CSF3R-T618 and Mpl-W515L normalized to vector control.
Figure 9A:
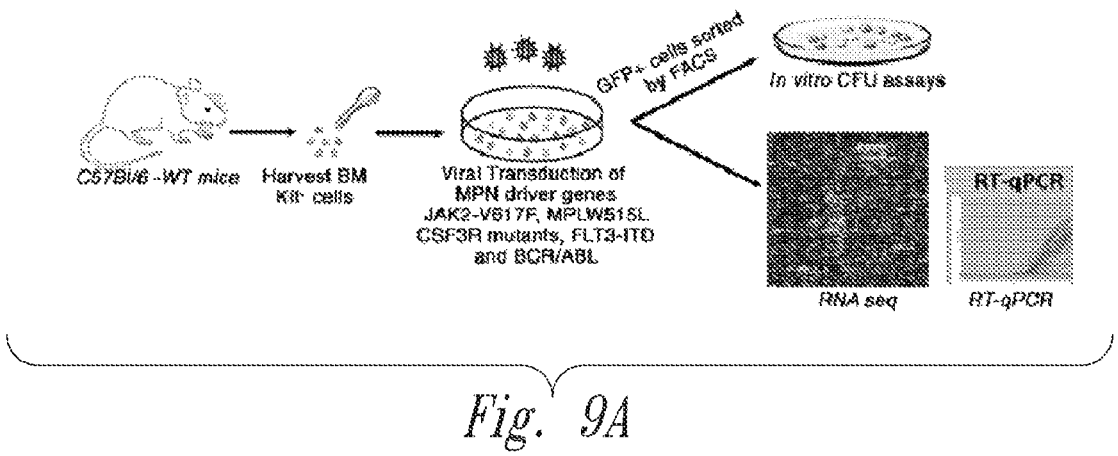
FIG. 9 shows the overexpression of DUSP1 in MPNs.
Figure 9B:
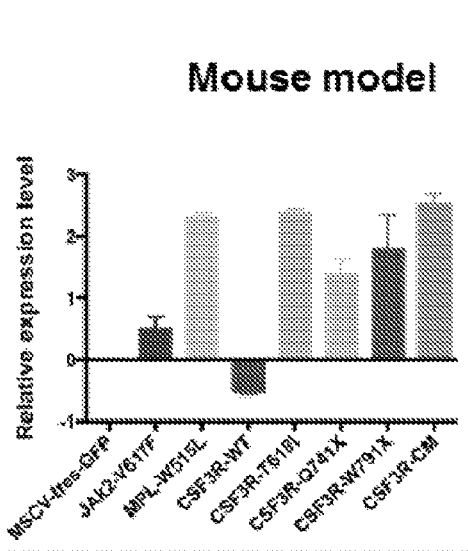
Figure 9C:
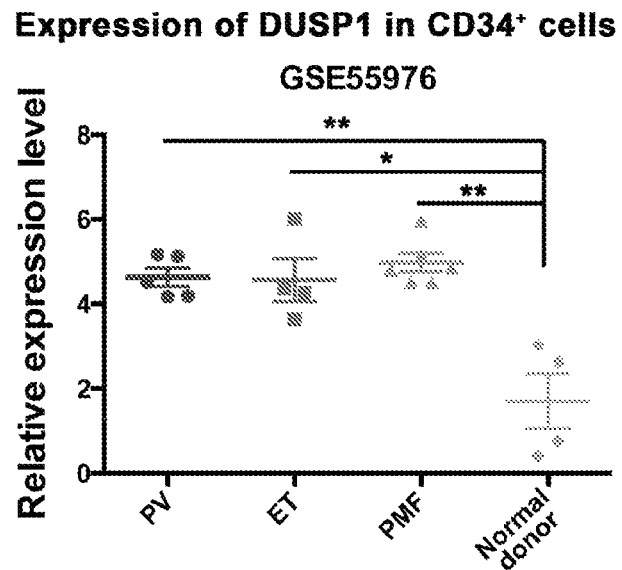

To test this, a comprehensive, whole genome expression analysis was performed using primary mouse bone marrow-derived Kit$^+$ cells transduced with MPD inducing oncogenes, Jak2-V617F, Mpl-W515L, CSF3R-T618I, BCR-ABL, Flt3-ITD); results are shown in FIG. 7: (A) Mice transplanted with WT bone marrow cells expressing different oncogenes showed robust leukemia onset after second week of transplantation. (B) Mice transplanted with Dusp1$^{-/-}$ bone marrow cells expressing different oncogenes showed lack of leukemia development. This analysis revealed that Dusp1/Mkp1 is overexpressed in all these MPN cells except the BCR-ABL positive cells. Dusp1, but not c-Fos, was overexpressed when compared with cells transduced with vector (pMSCV-Ires-GFP) or non-mutated gene; results are shown in FIG. 8. Likewise, MPD patients showed induced expression of DUSP1 but not the c-FOS, thus supporting the notion that the overexpression of DUSP1 can be responsible for the lack of TKI selectivity; results are shown in FIG. 9: (A) and (B) show the generation and results from the mouse model using C57BI/6 WT-mice. (C) shows the relative expression levels in patient samples. CD34+ cells from six patients representing each subtype were analyzed. P values: **=>0.001 and *=>0.01. This finding was then validated using Dusp1 knock-out mice, which revealed that the MPN-inducing genes, namely Jak2-V617F, Mpl-W515L, and CSF3R-T618I, are unable to induce leukemia in the absence of Dusp1 (FIG. 9B).

To test this, hematopoietic CFU assays were performed using mouse bone marrow-derived Kit+ cells transduced with retroviruses expressing, pMSCV-Ires-GFP (vector), Jak2-V617F-Ires-GFP, Mpl-W515L-ires-GFP, and CSF3R-T618IIres-GFP. Strikingly, CFU assays revealed that the Dusp1 deficiency induces synthetic lethality to MPD genes, in comparison to control (vector transduced cells); results are shown in FIGS. 10-12.

Figure 10A:
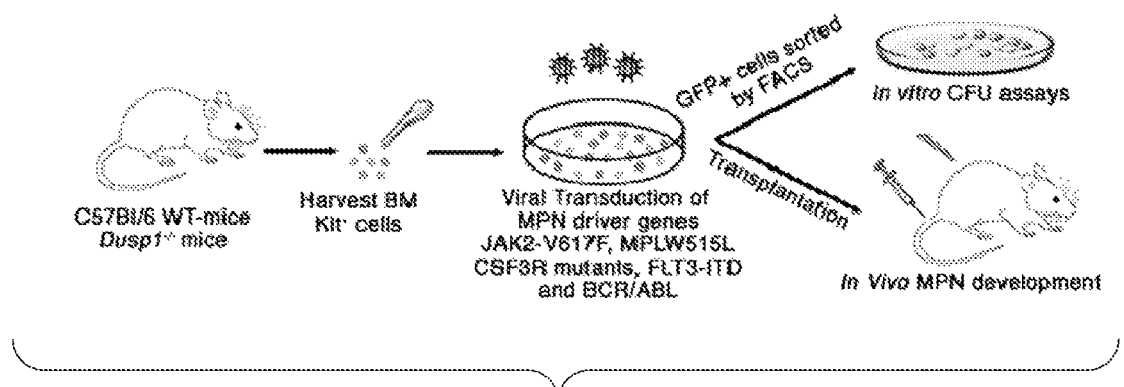
FIG. 10 shows that DUSP1 deficiency has synthetic lethality to MPN driver oncogenes.
Figure 10B:
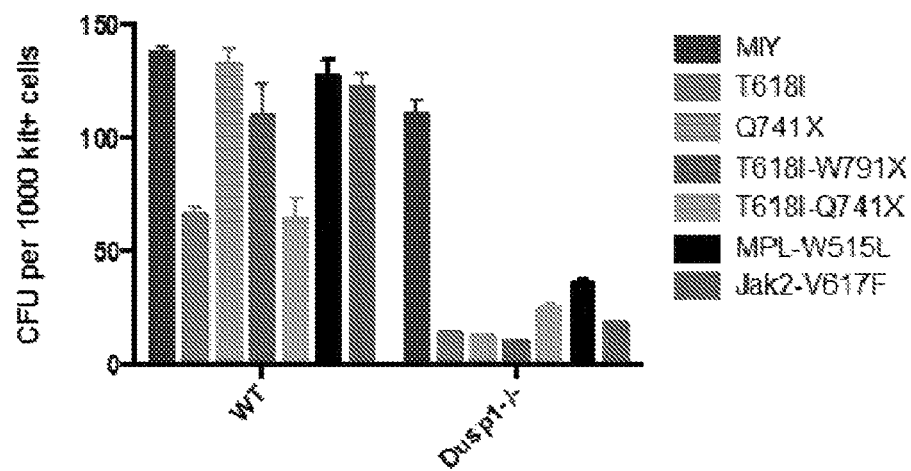

FIG. 10: (A) and (B) show the generation and results from the mouse model using C57BI/6 WT-mice and Dusp1$^{-/-}$ mice, with viral transduction of MPN driver genes JAK2-V617F, MPLW515L, and CSF3R mutants, FLT3-ITD, and BCR/ABL.

Figure 11A:
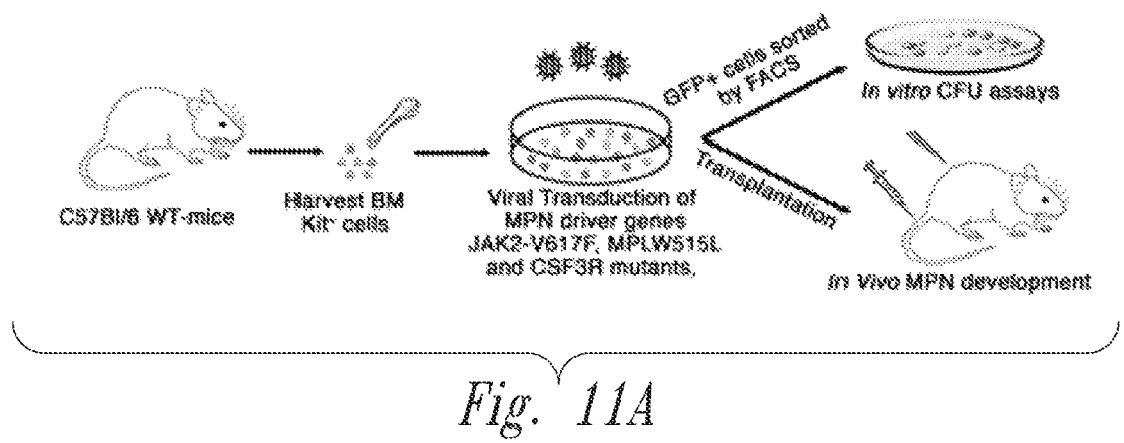
FIG. 11 shows that DUSP1 deficiency has synthetic lethality to MPN driver oncogenes, namely oncogenic CSF3R and Jak2-V617F.
Figure 11B:
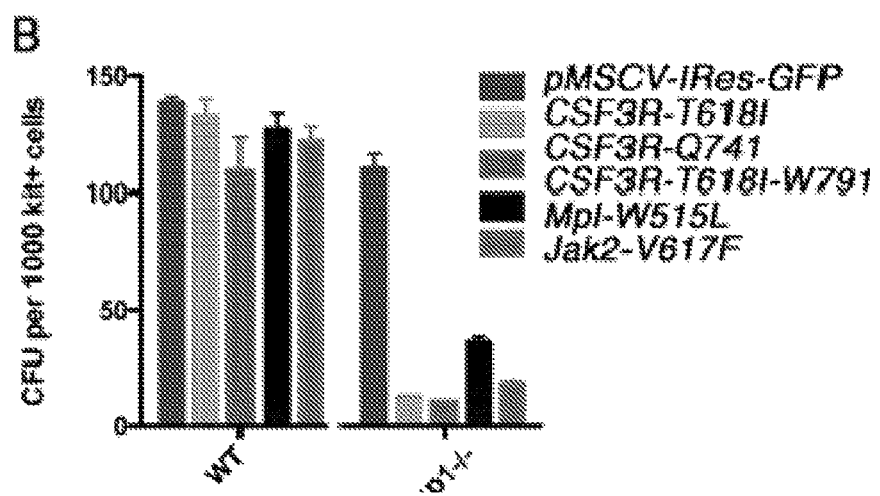

FIG. 11: (A) A schema for in vitro and in vivo assays, from the mouse model using C57BI/6 WT-mice and Dusp1$^{-/-}$ mice, with viral transduction of MPN driver genes JAK2-V617F, MPLW515L, and CSF3R mutants. (B) Bar graph showing significantly reduced colony numbers in the absence of Dusp1. (A) and (B) show the generation and results.

FIG. 12: BM derived Kit+ cells from wild type and Dusp1$^{-/-}$ mice were transduced with retroviruses expressing CSF3RT618I, CSF3R-T618I-W791X, MPL-W515L, and Jak2 V617F. (A) Mice transplanted with wild type cells showing robust leukemia development by CSF3R and Mpl mutants, while mice received Jak2-V617F cells showed mild elevation in WBC, but showed significant increase in red cells and reticulocytes. (B) Leukemic burden as GFP+ cells over a period of eight weeks. (C) Mice received cells lacking Dusp1 did not show any signs of leukemia. (D) All the GFP positive cells were abolished over the period of seven weeks in oncogenic conditions, while vector transduced cells have maintained normal engraftments. These data clearly show that lack of Dusp1 has synthetic lethality to MPD development.

Given the limitations of in vitro assays, performed in vivo experiments were then performed using bone marrow transduction transplantation assays. For in vivo analysis, mice were transplanted with 80-100 thousand bone marrow Kit$^+$ cells expressing Jak2-V617F-ires-GFP, CSF3R-T618I-Ires-GFP and MSCV-Ires-GFP (vector control). Mice received wild-type cells developed fatal MPD with a disease latency of 4-6 months. While deletion of Dusp1 did not develop disease, rather its deletion is synthetic lethal to expression of Jak2-V617F and CSF3R-T618I cells. In contrast, mice transplanted with vector transduced Kit$^+$ cells lacking Dusp1 showed normal engraftment, prolonged maintenance of transduced cells both in peripheral blood and bone marrow. Altogether, these data clearly demonstrate that Dusp1 mediates non-oncogene-addiction in MPD. Further studies with the Dusp1 inhibitor, BCI, showed selective targeting of MPN cells in vitro in a colony forming unit (CFU) assay.

Accordingly, BCI can be used for MPN treatment. In particular, BCI can be developed for oral administration for MPN patients, with improved PK and PD.

Example 6

Genetic Depletion of Dusp1 in Mouse Models of MPN

Based on the above observations, the role of Dusp1 in MPD driven by Mpl-W515L and Calreticulin was tested, as they have different clinical outcome and disease induction pathways. In addition, these experiments used the retroviral mouse model, which is expedient and cost effective to validate concepts. Because retroviruses are unable to target the quiescent and LT-HSCs, (LT-HSCs expressing JAk2-V617F represent quiescent LICs) it was indeterminate whether inhibition of Dusp1 will be effective in complete eradication of JAK2-V617F positive cells. Therefore, Applicant determined the effectiveness of Dusp1 inhibition in a transgenic mouse model of Jak2-V617F. Given the small molecule inhibitor for Dusp1 presently available, namely BCI, the subsequent study was designed to test its effectiveness in mouse models of MPD and in patient-derived mouse xenografts.

Genetic Depletion of Dusp1 in Jak2-V617F Knock-In Mouse Model.

The Jak2-V617F knock-in mouse model[70] of MPD was developed by Garry Gilliland. This mouse develops disease phenotypes (splenomegaly, high WBC count, and expansion of erythrocytes and platelets in 60 days). Importantly, the disease is transplantable with sorted hematopoietic stem cells (data not shown). Inducible Jak2-V617F transgenic mice have been generated with Dusp1 knockout by breeding the Jak2-V617F mice[70] with the Dusp1$^{-/-}$, in order to generate mice useful for the present studies. A competitive transplantation is performed using 104 Kit$^+$Lin$^-$Sca1$^+$ sorted cells from the transgenic mice C57BL/6 (CD 45.2) mixed with half a million of RBC depleted normal BM cells derived from recipient Boy/J mice (CD 45.1). After 4 weeks of transplantation, disease development is monitored bi-weekly using peripheral blood by taking the total blood counts using Hemavet. FACS analysis is performed to monitor the leukemic burden and expansion by measuring the levels of CD45.2 (leukemic) and normal (CD45.1) cells. Finally, analysis is performed for stem/progenitor cells from the bone marrow aspirates to quantify the leukemic burden and levels of LICs (BCR/ABL$^+$-Lin$^-$Kit$^+$Sca1$^+$) in control and experimental groups. For each condition, 10 mice are used.

Genetic Depletion of Dusp1 in MPL-W515L-Induced MPD

Given that there is no available MPL-W515L transgenic mouse, bone marrow transduction transplantation assays are used to test the effect of Dusp1 deficiency in this model. Bone marrow-derived Kit+ cells from both wild type and Dusp1−/− mice are transduced with lentiviruses expressing Mpl-W515L-Ires-GFP. Eighty to one hundred thousand GFP positive cells are transplanted in Boy/J mice with host-derived RBC deplete half a million bone marrow cells. After 4 weeks of transplantation, disease development is monitored bi-weekly using peripheral blood by taking the total blood counts using Hemavet. FACS analysis is performed to monitor the leukemic burden and expansion by measuring both levels GFP and CD45.2 (leukemic) and normal (CD45.1) cells. Finally, analysis for stem/progenitor cells from the bone marrow aspirates is performed to quantify the leukemic burden and levels of LICs (GFP+-Lin-Kit+Sca1+) in control and experimental groups. For each condition, 10 mice are used. Should any GFP+ cells be seen in the bone marrow at the end of four months after transplantation, secondary transplantation is performed to test its potential for disease development and to make sure that the LICs have been cleared.

Genetic Depletion of Dusp1 in Calr-Fs-Induced MPD

Bone marrow derived kit positive cells from both wild type and Dusp1$^{-/-}$ mice are transduced with lentiviruses expressing Calr-fs-ires-GFP. Most mutations in calreticulin are frameshift or deletion mutation in the exon9, which results into a novel c-terminal peptide in the Calreticulin proteins. Eighty to one hundred thousand GFP positive cells are transplanted in Boy/J mice with host derived RBC deplete half a million bone marrow cells. After 4 weeks of transplantation, disease development is monitored bi-weekly using peripheral blood by taking the total blood counts using Hemavet. FACS analysis is performed to monitor the leukemic burden and expansion by measuring both levels GFP and CD45.2 (leukemic) and normal (CD45.1) cells. Finally, analysis is performed for stem/progenitor cells from the bone marrow aspirates to quantify the leukemic burden and levels of LICs (GFP$^+$-Lin$^-$Kit$^+$Sca1$^+$) in control and experimental groups. For each condition, 10 mice are used. Should any GFP+ cells be seen in the bone marrow at the end of four months after transplantation, secondary transplantation is performed to test its potential for disease development and to make sure that the LICs have been cleared.

According to particular aspects, genetic inhibition of Dusp1 eliminates both the bulk of MPD disease, as well as quiescent LICs, as evidenced by a failure to secondary transplantation and relapse. Given the differences in molecular mechanisms utilized by these genes to induce disease, Mpl-W515L and Calr-fs may not show similar level of leukemic depletion as was observed with Jak2-V617F and CSF3R-T618I-induced MPD, given that the combination of Dusp1 and c-Fos is more efficient in eliminating the LICs in CML. The role of c-Fos, and its combination with Dusp1 and c-Fos, are tested first. Given the available mouse models in hand and chemical inhibitors, whether this combination is able to completely eradicate the MPD and LICs is readily tested.

However, the inherent differences in the biology of quiescent and proliferating LICs may not allow for the complete elimination of quiescent LICs. To address this, 14 genes (HIF1, ID1, ID2, CCND, CCNG2, DDIT3, DDIT4, IRAK2, TLR1, VEGF, GADD45A, GADD45B, Aquaporin, and STX11), are explored, which are commonly overexpressed in LICs of CM, MPD and TKI resistant Baf3-BCR-ABL and K562 cells. Pathway analysis by IPA revealed that these genes affect both cell proliferation and apoptotic pathways. The roles of CCNG2, and ID2 in combination with Dusp1 and c-Fos, are tested, as shRNA mediated knockdown of CCNG2 and ID2 showed increased sensitivity for imatinib, suggesting their combination with Dusp1 and c-Fos may be more efficient in eliminating quiescent LIC.

Example 7

Pharmacological Inhibition of Dusp1 was Demonstrated in Mouse Models of MPN

Both bulk of leukemia and leukemic stem cells from MPD overexpress Dusp1 (FIG. 8). Subsequent studies in mice showed lack of Dusp1 has synthetic lethality to Jak2-V617F and CSF3R-T618I driven MPD. According to particular aspects of the present invention, a key to successful targeted-therapy is the identification of critical, functional nodes in the oncogenic network, whose inhibition will cause the cessation of the malignant state either by cellular death or differentiation. According to additional aspects of the present invention, therapeutic agents targeting these nodes must display a sufficiently large therapeutic window with which to kill cancer cells, while sparing normal cells. In other words, the therapeutic agents must constitute "synthetic lethality" with the cancer genotype.[71] c-FOS and DUSP1 in AML should be targeted, as they constitute non-oncogene addiction (NOA) in kinase driven malignancies.[55] NOA is defined as the dependence of the cancerous state on the activities of a wide variety of genes and pathways, many of which are not inherently oncogenic and not mutated.[56] Importantly, these genes and pathways are essential to support the oncogenic phenotype of cancer cells but are not required to the same degree for the viability of normal cells. Therefore, these dependencies when inhibited constitute synthetic lethality with the underlying genetic context, thus providing a strong rationale to target Dusp1 in MPD patients. Altogether, these experiments will provide a basis for the future development of a clinical trial for curative treatment of both sensitive and de novo resistant CML patients.

A tractable model of MPD driven by Jak2-V617 knock-in, 5-10 thousand LSK (Lin$^-$, SCa1$^+$, and Kit$^+$) cells from this mouse are transplanted in Boy/J mice with half a million RBC depleted bone marrow cells from the recipient mice. Drug treatment begins after two weeks of transplantation. Mice are treated with BCI with a dose of 10 mg/kg/twice daily in PBS via intra-peritoneal injection. Mice are treated for 6-8 weeks, as in CML a 4-6 week treatment period is sufficient to eradicate leukemia. The effect of drug treatment is monitored weekly using peripheral blood by taking the total blood counts using Hemavet. FACS analysis is performed to monitor the leukemic burden and expansion by measuring levels of CD45.2 (leukemic) and normal (CD45.1) cells. Finally, analysis is performed for stem/progenitor cells from the bone marrow aspirates to quantify the leukemic burden and levels of LICs (Lin$^-$Kit$^+$Sca1$^+$) in control and experimental groups. For each condition, 10 mice are used. Mice showing less than 1% of CD45.2 positive cells at the end of treatment are considered negative, while mice that show persistence of CD45.2 positive above 1% are evaluated in secondary transplantation to make sure that the LICs have been cleared.

Bone marrow Kit$^+$ cells from wild-type C57Bl/6 mice are transduced with retroviruses expressing CSF3R-T618I, Mpl-W515L and Carl-fs. Eighty to one hundred thousand GFP positive cells are transplanted into irradiated Boy/J mice along with 0.5 million normal bone marrow cells from the wild-type recipient mice. After 2 weeks of transplantation, mice are treated with Dusp1 inhibitor, BCI. Mice are treated for 6-8 weeks with BCI at a dose of 10 mg/kg/twice daily in PBS via intra peritoneal injection. The effect of drug treatment is monitored weekly using peripheral blood by taking the total blood counts using Hemavet. FACS analysis is performed to monitor the leukemic burden and expansion by measuring both levels GFP and CD45.2 (leukemic) and normal (CD45.1) cells. Finally, analysis is performed for stem/progenitor cells from the bone marrow aspirates to quantify the leukemic burden and levels of LICs (GFP$^+$-Lin$^-$Kit$^+$Sca1$^+$) in control and experimental groups. For each condition, 10 mice are used. Mice showing less than 1% of GFP positive cells at the end of treatment are considered negative, while mice that show persistence of CD45.2 positive cells above 1% are evaluated in secondary transplantation to make sure that the LICs have been cleared.

A key to successful targeted-therapy is the identification of critical, functional nodes in the oncogenic network whose inhibition will cause the cessation of the malignant state either by cellular death or differentiation. Therapeutic agents targeting of these nodes must display a sufficiently large therapeutic window with which to kill cancer cells, while sparing normal cells. In other words, the therapeutic agents must constitute "synthetic lethality" with the cancer genotype.[71] The preliminary data show that DUSP1 constitutes non-oncogene addiction in CML. Importantly, non-oncogene addiction genes and pathways are essential to support the oncogenic phenotype of cancer cells but are not required to the same degree for the viability of normal cells.[56] Therefore, these dependencies when inhibited constitute synthetic lethality with the underlying tumor genotype[12]. It is expected that inhibition of Dusp1 will constitute synthetic lethality in Jak2-V617F, Mpl-W515L, Calr-fs and CSF3R-T618 driven MPD. However, pharmacological inhibition often times unable to replicate genetic inhibition for many reasons, such as inefficient binding, poor bioavailability and targeting several other proteins, as small molecule inhibitors are exclusive as genetic knockout. Given the study with BCI in mouse model of CML that it is bioavailable and inhibits its designated target; however, one cannot rule out its off-target binding induced survival pathways in the context of MPD.

Figure 13A:
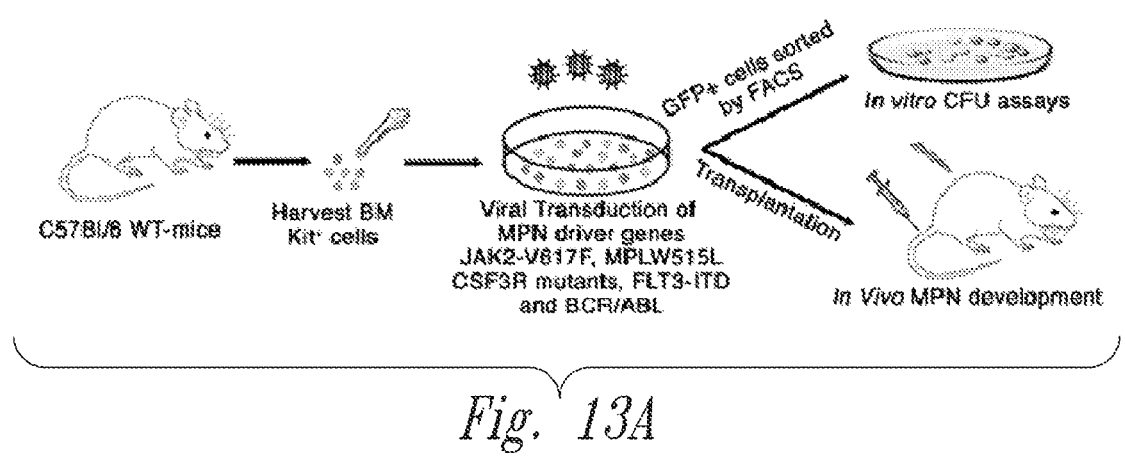
FIG. 13 shows that ruxolitinib and BCI eradicate the MPL and CSF3R-driven leukemia.
Figure 13B:
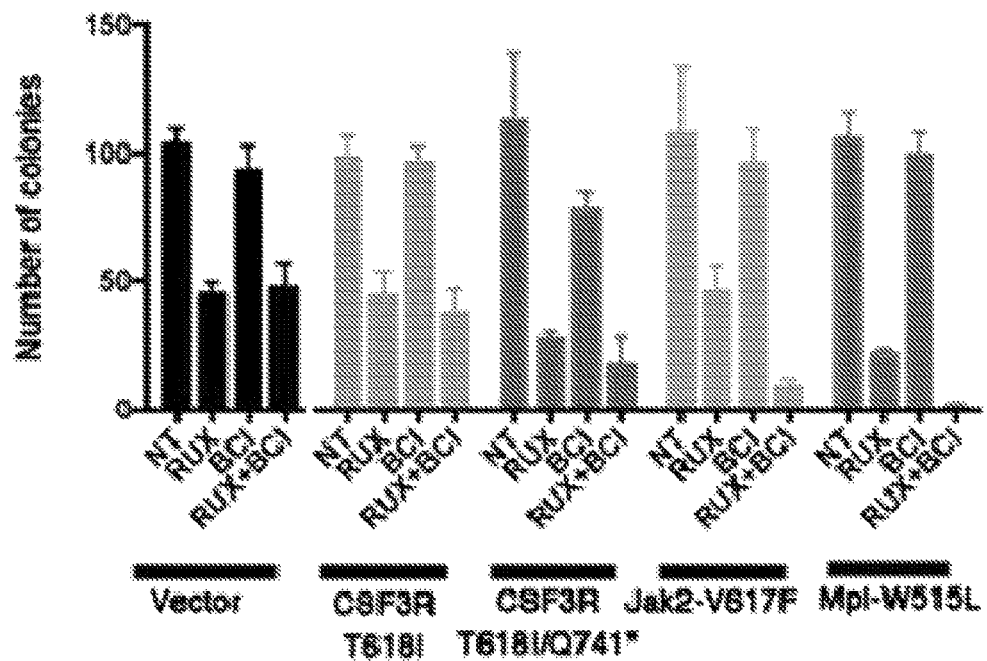

To address this, the combination of BCI with Fos inhibitor and finally with TKI (ruxolitinib+BCI, ruxolitinib+DFC and ruxolitinib+BCI+DFC) was tested. Given the potent selectivity of DFC+BCI+imatinib on the LICs of CML, it is anticipated that a combination of either DFC+BCI or DFC+BCI+ruxolitinib can eliminate MPD and its LICs. In fact, ruxolitinib and BCI were shown to eradicate the MPL and CSF3R driven leukemic cells; results are shown in FIG. 13.

Example 8

Efficacy of Genetic and Chemical Inhibition of DUSP1 in Human MPD was Established TKI treatment in MPD driven by mutations in JAK2, MPL and CSF3R is not curative, and most patients relapse within few months. Leukemic stem cells in MPD induce the expression of DUSP1 (FIG. 8), thus provides a strong rationale to target DUSP1 in MPD patients. While the preceding experiments establish the proof of concept to target DUSP1 in this group of blood diseases, in order to translate to human application, the inhibition of DUSP1 in MPD patient-derived cells is tested. These experiments provide a basis for the future development of a clinical trial for curative treatment of MPD. 11 MPD patient samples (5 PV, 3 ET and 3 PMF) have been acquired, and more are obtained.

Testing the Genetic Inhibition of DUSP1 in Primary Patient Derived CD34+ Cells

CD34$^+$ cells are isolated from patient-derived BM or peripheral blood cells. These purified CD34$^+$ cells are used for therapeutic and genetic evaluation both in vitro and in vivo. CD34$^+$ cells are isolated using human-CD34 MicroBead Kit from Milteny. Two to three million CD34$^+$ cells are transduced with lentiviruses expressing shRNAs for DUSP1 and control (scrambled-Sc-shRNA). These hairpins have been cloned in a modified pLKO1 lentiviral vectors (pLKO-DUSP1:shRNA-CMV-venus and pLKO1-Sc:shRNA-CMVvenus), to aid in FACS mediated sorting. Transduced cells are sorted by FACS using venus as marker. These cells are grown in liquid culture overnight (IL-3, IL-6, G-CSF, Flt3-LG, SCF and EPO) in SFEM (Stem cell) media. Ten thousand CD34+ cells are plated in triplicate in methocult-H4034 (STEMCELL Tech.) for each hairpins, CFU number is determined after two weeks of plating. Total RNA and crude protein extract are prepared from remaining cells to quantify DUSP1 by both Q-PCR and immunoblotting. Likewise, CD34+ cells from normal donors are evaluated as control.

Testing the Chemical Inhibition of DUSP1 in Primary Patient Derived CD34+ Cells.

Ten thousand CD34$^+$ cells are plated in triplicate for each drug conditions (ruxolitinib, and BCI,) using methocult-H4034 supplemented with growth factors. CFU number is counted after two weeks of plating to determine the cytotoxic effect of each drugs and their effect in combination. In parallel, CD34$^+$ cells from normal healthy donor are used as a control. For in vivo evaluation, three million CD34$^+$ cells from PMF patient are transplanted into sub-lethally irradiated 8-week-old NSG mice. CD34$^+$ cells from PV and ET do not survive as most mice lose engrafts within 3-4 weeks, with observation of robust engraftments and expansion with PMF cells, and subsequently these mice develop splenomegaly (data not shown). Thirty-mice for each patients are transplanted, after two weeks of transplantation, leukemic engraftments are determined on bone marrow biopsies by FACS using mouse- and human-specific antibodies against CD45. Mice are then grouped into four different cohorts (n=10/group, five females and five males) for drug treatments with vehicle (PBS), BCI, ruxolitinib. Ruxolitinib and vehicle treated mice are used as controls. Mice that showed less than two percent of hCD45 levels are excluded from the study. Drugs are given twice by intra-peritoneal injection in PBS having dosage for BCI (10 mg/kg) and ruxolitinib (50 mg/kg). Leukemic burden is determined every two weeks, while percentage of stem progenitor populations is determined at the end of treatment by FACS to quantify the survival and eradication of LICs. To determine the drug induced cell death, apoptotic cell death is measured by AnnexinV/7AAD staining of BM cells using FACS. Likewise, LICs is measured by staining with CD34$^+$ and CD38$^-$ and CD90$^+$ specific antibodies. To make sure that leukemic cells and LICs are completely eradicated, drug treatment is stopped after four weeks of treatment in mice that showed depleted or eradicated LICs in BM biopsies, as treatment discontinuation reestablishes disease if these mice have been left with residual LICs. In addition, secondary transplantation from these mice is performed to make sure that the LICs have been cleared. A definitive assay to measure LIC content is the limiting dilution transplantation assay. LIC content of the AML samples is measured by limiting dilution transplantation assays using PMF cells treated with inhibitors vs PBS (vehicle). 8 mice are transplanted per dilution, ranging from 100 cells to 1×10$^6$ cells in 10-fold increments. Mice are monitored for leukemia development, and LIC frequency is estimated by Poisson distribution statistics.

Example 9

Therapeutic Targeting of DUSP1 in MPN: A Curative Strategy

According to particular aspects, inhibition of DUSP1 constitutes synthetic lethality in MPD cells. According to additional aspects, additional targets shown to sensitize the LICs in CML are targeted, in addition to c-FOS, such as HIF1, ID1, ID2, CCND, CCNG2, DDIT3, DDIT4, IRAK2, TLR1, VEGF, GADD45A, GADD45B, Aquaporin, and STX11. For example, DFC and echinomycin are small molecule inhibitors of c-Fos and HIf1, respectively Because the Fos/Dusp1 knock-out mice are viable and healthy, and no adverse effects were observed after deletion of both genes, both of these genes represent a good target for drug development.

In some embodiments of the invention, DUSP1 inhibitors are used alone or in combination with at least one other inhibitor of a kinase to treat MPN. In some embodiments, the kinase inhibitor inhibits a kinase selected from the group consisting of c-FOS, such as HIF1, ID1, ID2, CCND, CCNG2, DDIT3, DDIT4, IRAK2, TLR1, VEGF, GADD45A, GADD45B, Aquaporin, and STX11. In some embodiments, the kinase inhibitor is selected from the group consisting of DFC and echinomycin.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the invention extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the invention. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

REFERENCES

1 Levine, R. L. et al. Activating mutation in the tyrosine kinase JAK2 in polycythemia vera, essential thrombocythemia, and myeloid metaplasia with myelofibrosis. *Cancer Cell* 7, 387-397 (2005).
2 Baxter, E. J. et al. Acquired mutation of the tyrosine kinase JAK2 in human myeloproliferative disorders. *Lancet* 365, 1054-1061, doi:S0140-6736(05)71142-9 [pii] 10.1016/S0140-6736(05)71142-9 (2005).
3 James, C. et al. A unique clonal JAK2 mutation leading to constitutive signalling causes polycythaemia vera. *Nature* 434, 1144-1148, doi:nature03546 [pii]10.1038/nature03546 (2005).
4 Kralovics, R. et al. A gain-of-function mutation of JAK2 in myeloproliferative disorders. *N Engl J Med* 352, 1779-1790, doi:352/17/1779 [pii] 10.1056/NEJMoa051113 (2005).
5 Verstovsek, S. et al. Safety and efficacy of INCB018424, a JAK1 and JAK2 inhibitor, in myelofibrosis. *N Engl J Med* 363, 1117-1127, doi:10.1056/NEJMoa1002028 (2010).
6 Tefferi, A. JAK inhibitors for myeloproliferative neoplasms: clarifying facts from myths. *Blood* 119, 2721-2730, doi:10.1182/blood-2011-11-395228 (2012).
7 Tefferi, A. Challenges facing JAK inhibitor therapy for myeloproliferative neoplasms. *N Engl J Med* 366, 844-846, doi:10.1056/NEJMe1115119 (2012).
8 Heine, A. et al. The JAK-inhibitor ruxolitinib impairs dendritic cell function in vitro and in vivo. *Blood* 122, 1192-1202, doi:10.1182/blood-2013-03-484642 (2013).
9 Tefferi, A. Ruxolitinib targets DCs: for better or worse? *Blood* 122, 1096-1097, doi:10.1182/blood-2013-07-509612 (2013).
10 Sawyers, C. L. Shifting paradigms: the seeds of oncogene addiction. *Nat Med* 15, 1158-1161, doi:10.1038/nm1009-1158 (2009).
11 Weinstein, I. B. Cancer. Addiction to oncogenes—the Achilles heal of cancer. *Science* 297, 63-64, doi:10.1126/science.1073096 (2002).
12 Pagliarini, R., Shao, W. & Sellers, W. R. Oncogene addiction: pathways of therapeutic response, resistance, and road maps toward a cure. *EMBO reports* 16, 280-296, doi:10.15252/embr.201439949 (2015).
13 Savona, M. & Talpaz, M. Getting to the stem of chronic myeloid leukaemia. *Nat Rev Cancer* 8, 341-350, doi:10.1038/nrc2368 (2008).
14 Jiang, X. et al. Properties of CD34+ CML stem/progenitor cells that correlate with different clinical responses to imatinib mesylate. *Blood* 116, 2112-2121, doi:blood-2009-05-222471 [pii] 10.1182/blood-2009-05-222471.
15 Jiang, X. et al. Primitive interleukin 3 null hematopoietic cells transduced with BCR-ABL show accelerated loss after culture of factor-independence in vitro and leukemogenic activity in vivo. *Blood* 100, 3731-3740, doi:10.1182/blood-2002-05-1324 2002-05-1324 [pii] (2002).
16 Jiang, X., Saw, K. M., Eaves, A. & Eaves, C. Instability of BCR-ABL gene in primary and cultured chronic myeloid leukemia stem cells. *J Natl Cancer Inst* 99, 680-693, doi:99/9/680 [pii] 0.1093/jnci/djk150 (2007).
17 Jiang, X., Smith, C., Eaves, A. & Eaves, C. The challenges of targeting chronic myeloid leukemia stem cells. *Clin Lymphoma Myeloma* 7 Suppl 2, S71-80 (2007).
18 Corbin, A. S. et al. Human chronic myeloid leukemia stem cells are insensitive to imatinib despite inhibition of BCR-ABL activity. *J Clin Invest* 121, 396-409, doi:10.1172/JCI35721 (2011).
19 Wilson, T. R. et al. Widespread potential for growth-factor-driven resistance to anticancer kinase inhibitors. *Nature* 487, 505-509, doi:10.1038/nature11249 (2012).
20 Straussman, R. et al. Tumour micro-environment elicits innate resistance to RAF inhibitors through HGF secretion. *Nature* 487, 500-504, doi:10.1038/nature11183 (2012).

21 Daley, G. Q., Van Etten, R. A. & Baltimore, D. Induction of chronic myelogenous leukemia in mice by the P210bcr/abl gene of the Philadelphia chromosome. *Science* 247, 824-830 (1990).

22 Daley, G. Q., Van Etten, R. A. & Baltimore, D. Blast crisis in a murine model of chronic myelogenous leukemia. *Proc Natl Acad Sci USA* 88, 11335-11338 (1991).

23 Scott, M. L., Van Etten, R. A., Daley, G. Q. & Baltimore, D. v-abl causes hematopoietic disease distinct from that caused by bcr-abl. *Proc Natl Acad Sci USA* 88, 6506-6510 (1991).

24 Druker, B. J. et al. Efficacy and safety of a specific inhibitor of the BCRABL tyrosine kinase in chronic myeloid leukemia. *N. Engl. J. Med.* 344, 1031-1037 (2001).

25 Druker, B. J. et al. Effects of a selective inhibitor of the Abl tyrosine kinase on the growth of Bcr-Abl positive cells. *Nat Med* 2, 561-566 (1996).

26 Noble, M. E., Endicott, J. A. & Johnson, L. N. Protein kinase inhibitors: insights into drug design from structure. *Science* 303, 1800-1805 (2004).

27 Sawyers, C. L. Opportunities and challenges in the development of kinase inhibitor therapy for cancer. *Genes Dev* 17, 2998-3010 (2003).

28 Azam, M. & Daley, G. Q. Anticipating clinical resistance to target-directed agents: the BCR-ABL paradigm. *Mot Diagn Ther* 10, 67-76 (2006).

29 Azam, M., Latek, R. R. & Daley, G. Q. Mechanisms of autoinhibition and STI-571/imatinib resistance revealed by mutagenesis of BCR-ABL. *Cell* 112, 831-843 (2003).

30 Azam, M. et al. Activity of dual SRC-ABL inhibitors highlights the role of BCR/ABL kinase dynamics in drug resistance. *Proc Natl Acad Sci USA* 103, 9244-9249 (2006).

31 Azam, M., Seeliger, M. A., Gray, N. S., Kuriyan, J. & Daley, G. Q. Activation of tyrosine kinases by mutation of the gatekeeper threonine. *Nat Struct Mol Biol* 15, 1109-1118, doi:nsmb.1486 [pii] 10.1038/nsmb.1486 (2008).

32 Druker, B. J. et al. Activity of a specific inhibitor of the BCR-ABL tyrosine kinase in the blast crisis of chronic myeloid leukemia and acute lymphoblastic leukemia with the Philadelphia chromosome. *N Engl J Med* 344, 1038-1042, doi:10.1056/NEJM200104053441402 (2001).

33 Gorre, M. E. et al. Clinical resistance to STI-571 cancer therapy caused by BCR-ABL gene mutation or amplification. *Science* 293, 876-880, doi:10.1126/science.1062538 (2001).

34 Sawyers, C. Targeted cancer therapy. *Nature* 432, 294-297 (2004).

35 Sawyers, C. L. Even better kinase inhibitors for chronic myeloid leukemia. *N Engl J Med* 362, 2314-2315, doi: NEJMe1004430 [pii] 10.1056/NEJMe1004430.

36 Crossman, L. C. et al. hOCT 1 and resistance to imatinib. *Blood* 106, 1133-1134; author reply 1134, doi:106/3/1133 [pii] 10.1182/blood-2005-02-0694 (2005).

37 Quintas-Cardama, A., Kantarjian, H. & Cortes, J. Flying under the radar: the new wave of BCR-ABL inhibitors. *Nature reviews. Drug discovery* 6, 834-848, doi:10.1038/nrd2324 (2007).

38 Shah, N. P. et al. Multiple BCR-ABL kinase domain mutations confer polyclonal resistance to the tyrosine kinase inhibitor imatinib (STI571) in chronic phase and blast crisis chronic myeloid leukemia. *Cancer Cell* 2, 117-125 (2002).

39 Roumiantsev, S. et al. Clinical resistance to the kinase inhibitor STI-571 in chronic myeloid leukemia by mutation of Tyr-253 in the Abl kinase domain P-loop. *Proc Natl Acad Sci USA* 99, 10700-10705, doi:10.1073/pnas.162140299 (2002).

40 Ross, D. M. & Hughes, T. P. How I determine if and when to recommend stopping tyrosine kinase inhibitor treatment for chronic myeloid leukaemia. *Br J Haematol* 166, 3-11, doi:10.1111/bjh.12892 (2014).

41 Li, X. et al. Bone marrow microenvironment confers imatinib resistance to chronic myelogenous leukemia and oroxylin A reverses the resistance by suppressing Stat3 pathway. *Archives of toxicology* 89, 121-136, doi: 10.1007/s00204-014-1226-6 (2015).

42 Quintas-Cardama, A. et al. Detection of dormant chronic myeloid leukemia clones in the bone marrow of patients in complete molecular remission. *Clinical lymphoma, myeloma & leukemia* 13, 681-685, doi:10.1016/j.clml.2013.07.010 (2013).

43 O'Hare, T., Zabriskie, M. S., Eiring, A. M. & Deininger, M. W. Pushing the limits of targeted therapy in chronic myeloid leukaemia. *Nat Rev Cancer* 12, 513-526, doi: 10.1038/nrc3317 (2012).

44 Sakamoto, Y. et al. Monitoring twenty-six chronic myeloid leukemia patients by BCR-ABL mRNA level in bone marrow: a single hospital experience. *Acta medica Okayama* 65, 335-342 (2011).

45 Pavlovsky, C. et al. Molecular monitoring of imatinib in chronic myeloid leukemia patients in complete cytogenetic remission: does achievement of a stable major molecular response at any time point identify a privileged group of patients? A multicenter experience in Argentina and Uruguay. *Clinical lymphoma, myeloma & leukemia* 11, 280-285, doi:10.1016/j.clml.2011.03.016 (2011).

46 Bartley, P. A. et al. Sensitive detection and quantification of minimal residual disease in chronic myeloid leukaemia using nested quantitative PCR for BCR-ABL DNA. *International journal of laboratory hematology* 32, e222-228, doi:10.1111/j 0.1751-553X.2010.01236.x (2010).

47 Asnafi, V. et al. Prediction of relapse by day 100 BCR-ABL quantification after allogeneic stem cell transplantation for chronic myeloid leukemia. *Leukemia* 20, 793-799, doi:10.1038/sj.leu.2404170 (2006).

48 Hess, G. et al. Sustained complete molecular remissions after treatment with imatinib-mesylate in patients with failure after allogeneic stem cell transplantation for chronic myelogenous leukemia: results of a prospective phase II open-label multicenter study. *J Clin Oncol* 23, 7583-7593, doi:10.1200/JCO.2005.01.3110 (2005).

49 Kesarwani, M. et al. Targeting substrate-site in Jak2 kinase prevents emergence of genetic resistance. *Scientific reports* 5, 14538, doi:10.1038/srep14538 (2015).

50 Krause, D. S. & Van Etten, R. A. Tyrosine kinases as targets for cancer therapy. *N Engl J Med* 353, 172-187, doi:10.1056/NEJMra044389 (2005).

51 M. Talpaz et al. Phase I trial of AP24534 in patients with refractory chronic myeloid leukemia (CML) and hematologic malignancies. *J Clin Oncol* 28 (2010).

52 Roberts, K. G. et al. Targetable kinase-activating lesions in Ph-like acute lymphoblastic leukemia. *N Engl J Med* 371, 1005-1015, doi:10.1056/NEJMoa1403088 (2014).

53 Zhang, J., Yang, P. L. & Gray, N. S. Targeting cancer with small molecule kinase inhibitors. *Nat Rev Cancer* 9, 28-39, doi:10.1038/nrc2559 (2009).

54 O'Hare, T. et al. AP24534, a pan-BCR-ABL inhibitor for chronic myeloid leukemia, potently inhibits the T315I mutant and overcomes mutationbased resistance. *Cancer Cell* 16, 401-412, doi:S1535-6108(09)00339-0 [pii] 10.1016/j.ccr.2009.09.028 (2009).

55 Luo, J., Solimini, N. L. & Elledge, S. J. Principles of cancer therapy: oncogene and non-oncogene addiction. *Cell* 136, 823-837, doi:10.1016/j.cell.2009.02.024 (2009).
56 Solimini, N. L., Luo, J. & Elledge, S. J. Non-oncogene addiction and the stress phenotype of cancer cells. *Cell* 130, 986-988, doi:10.1016/j.cell.2007.09.007 (2007).
57 Sharma, S. V., Fischbach, M. A., Haber, D. A. & Settleman, J. "Oncogenic shock": explaining oncogene addiction through differential signal attenuation. *Clin Cancer Res* 12, 4392s-4395s, doi:12/14/4392s [pii] 10.1158/1078-0432.CCR-06-0096 (2006).
58 Sharma, S. V. et al. A common signaling cascade may underlie "addiction" to the Src, BCR-ABL, and EGF receptor oncogenes. *Cancer Cell* 10, 425-435, doi:S1535-6108(06)00292-3 [pii] 10.1016/j.ccr.2006.09.014 (2006).
59 Sharma, S. V. & Settleman, J. Oncogenic shock: turning an activated kinase against the tumor cell. *Cell Cycle* 5, 2878-2880, doi:3598 [pii] (2006).
60 Sharma, S. V. & Settleman, J. Oncogene addiction: setting the stage for molecularly targeted cancer therapy. *Genes Dev* 21, 3214-3231, doi:10.1101/gad.1609907 (2007).
61 Bruennert, D. et al. Early in vivo changes of the transcriptome in Philadelphia chromosome-positive CD34+ cells from patients with chronic myelogenous leukaemia following imatinib therapy. *Leukemia* 23, 983-985, doi: leu2008337 [pii] 10.1038/leu.2008.337 (2009).
62 Dorfman, K. et al. Disruption of the erp/mkp-1 gene does not affect mouse development: normal MAP kinase activity in ERP/MKP-1-deficient fibroblasts. *Oncogene* 13, 925-931 (1996).
63 Zhang, J. et al. c-fos regulates neuronal excitability and survival. *Nat Genet* 30, 416-420, doi:10.1038/ng859 (2002).
64 Zhao, C. et al. Hedgehog signalling is essential for maintenance of cancer stem cells in myeloid leukaemia. *Nature* 458, 776-779, doi:10.1038/nature07737 (2009).
65 Molina, G. et al. Zebrafish chemical screening reveals an inhibitor of Dusp6 that expands cardiac cell lineages. *Nature chemical biology* 5, 680-687, doi:10.1038/nchembio.190 (2009).
66 Padhye, S. et al. Fluorocurcumins as cyclooxygenase-2 inhibitor: molecular docking, pharmacokinetics and tissue distribution in mice. *Pharmaceutical research* 26, 2438-2445, doi:10.1007/s11095-009-9955-6 (2009).
67 Huang, T. S., Lee, S. C. & Lin, J. K. Suppression of c-Jun/AP-1 activation by an inhibitor of tumor promotion in mouse fibroblast cells. *Proc Natl Acad Sci USA* 88, 5292-5296 (1991).
68 Park, S., Lee, D. K. & Yang, C. H. Inhibition of fos-jun-DNA complex formation by dihydroguaiaretic acid and in vitro cytotoxic effects on cancer cells. *Cancer letters* 127, 23-28 (1998).
69 Padhye, S. et al. New difluoro Knoevenagel condensates of curcumin, their Schiff bases and copper complexes as proteasome inhibitors and apoptosis inducers in cancer cells. *Pharmaceutical research* 26, 1874-1880, doi: 10.1007/s11095-009-9900-8 (2009).
70 Koschmieder, S. et al. Inducible chronic phase of myeloid leukemia with expansion of hematopoietic stem cells in a transgenic model of BCR-ABL leukemogenesis. *Blood* 105, 324-334, doi:10.1182/blood-2003-12-4369 2003-12-4369 [pii] (2005).
71 Kaelin, W. G., Jr. The concept of synthetic lethality in the context of anticancer therapy. *Nat Rev Cancer* 5, 689-698, doi:nrc1691 [pii] 10.1038/nrc1691 (2005).

The invention claimed is:
1. A method of treating a myeloproliferative neoplasm (MPN) or a symptom thereof, comprising administering, to a subject in need thereof, a therapeutically effective amount of one or more DUSP1 inhibiting compounds, or a pharmaceutically acceptable salt, ester, or prodrug thereof, wherein the MPN is driven by mutation in one or more oncogenes selected from the group consisting of Jak2, MPL, and CSFR3.
2. The method of claim 1, wherein the compound is selected from the group consisting of (E)-2-benzylidene-3-(cyclohexylamino)-2,3-dihydro-1H-inden-1-one (BCI), and sanguinarine.
3. The method of claim 1, wherein the compound is selected from the group consisting of BCI, BCI-164, BCI-165, BCI-11, BCI-8, BCI-9, BCI-211, BCI-212, BCI-303, BCI-183, BCI-297, BCI-216, BCI-215, BCI-256, BCI-269, BCI-304, BCI-296, BCI-299, BCI-10, sanguinarine, chelerythrine, hydroxychelidonine, berberine, tetrahydroberberine, and protopine.
4. The method of claim 3, wherein the compound is a BCI compound.
5. The method of claim 4, wherein the BCI compound has the general structure of Formula (I):

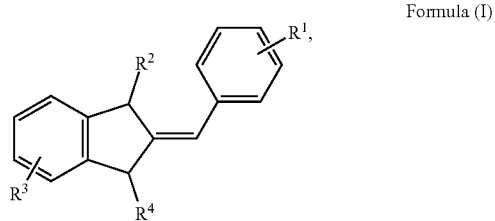

Formula (I)

wherein:
  $R^1$ is H, halogen, substituted or unsubstituted straight or branched chain C1-8 alkyl, substituted or unsubstituted straight or branched chain C1-8 heteroalkyl, or —CN;
  $R^2$ is —NR'R", wherein R' and R" can optionally be joined together to form a ring;
  $R^3$ is H, halogen, substituted or unsubstituted straight or branched chain C1-8 alkyl, substituted or unsubstituted straight or branched chain C1-8 heteroalkyl, or —CN;
  $R^4$ is =O or —OH; and
  R' and R" independently are H, halogen, substituted or unsubstituted straight or branched chain C1-8 alkyl, substituted or unsubstituted straight or branched chain C1-8 heteroalkyl, substituted or unsubstituted C3-8 cycloalkyl, substituted or unsubstituted C3-8 heterocycloalkyl, or substituted or unsubstituted C5-12 heteroaryl.
6. The method of claim 3, wherein the compound is a sanguinarine compound.
7. The method of claim 6, wherein the sanguinarine compound has the general structure of Formula (II):

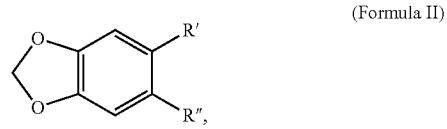

(Formula II)

wherein:

R' and R" are joined in a ring fused to the general core structure and are 1-4 saturated or unsaturated, substituted or unsubstituted fused ring systems fused to the general core structure represented in Formula (II), wherein each ring comprises 4-12 atoms, and wherein said atoms of the fused ring systems independently are carbon, nitrogen, oxygen, silicon, phosphorous, or sulfur, and wherein substituent groups for the fused ring systems are independently hydrogen, halogen, substituted or unsubstituted straight or branched chain C1-8 alkyl, substituted or unsubstituted straight or branched chain C1-8 heteroalkyl, substituted or unsubstituted C3-8 cycloalkyl, substituted or unsubstituted C3-8 heterocycloalkyl, =O, —OH, or —CN.

8. The method of claim 1, wherein the MPN comprises one or more disease or condition selected from the group consisting of polycythemia vera (PV), essential thrombocytosis (ET), primary myelofibrosis (PMF), chronic neutrophilic leukemia (CNL), systemic mastocytosis, hypereosinophilic syndrome, chronic myelomonocytic leukemia, and chronic eosinophilic leukemia.

9. The method of claim 1, wherein the DUSP1 inhibitor is an inhibitor of the Dusp1 gene and/or the Dusp1 protein.

10. The method of claim 1, further comprising combination therapy wherein the combination therapy comprises administration of at least one additional therapeutic agent to the patient and/or wherein the combination therapy comprises at least one therapy selected from the group consisting of surgery, chemotherapy, and radiation.

11. The method of claim 10, wherein the at least one additional therapeutic agent is selected from the group consisting of a tyrosine kinase inhibitor (TKI), a c-Fos inhibitor, a JAK kinase inhibitor, a MKP inhibitor, a PTP inhibitor, hydroxyurea.

12. The method of claim 11, wherein the TKI is an inhibitor of a tyrosine kinase gene and/or a tyrosine kinase protein.

13. The method of claim 11, wherein the c-Fos inhibitor is an inhibitor of the c-Fos gene and/or the c-Fos protein.

14. The method of claim 11, wherein the JAK kinase inhibitor is selected from the group consisting of ruxolitinib, CYT387, BMS911543, SAR302503BBT594, TG101348, CHZ868, and pacritinib.

15. The method of claim 11, wherein the MKP inhibitor is selected from the group consisting of sanguinarine, chelerythrine, hydroxychelidonine, berberine, tetrahydroberberine, protopine, and NSC-95397.

16. The method of claim 11, wherein the PTP inhibitor is selected from the group consisting of TPI-1, TPI-2, TPI-3, TPI-4, TPI-5, TPI-6, TPI-7, TPI-8, TPI-9, TPI-10, TPI-11 triptolide, and (5R)-5-hydroxytriptolide (LLDT-8).

17. The method of claim 1, wherein the compound is administered orally.

18. The method of claim 1, wherein the compound is administered to the subject over a treatment course selected from the group consisting of up to 10 days, 10 days to one month, one month to 6 months, 6 months to one year, one year to two years, and longer than two years.

19. The method of claim 1, wherein the method is part of a treatment monitoring protocol.

20. The method of claim 19, wherein the treatment monitoring protocol comprises obtaining MPN tissue from the patient and analyzing the tissue for DUSP1 activity.

* * * * *